US009974523B2

(12) United States Patent
Hibner et al.

(10) Patent No.: US 9,974,523 B2
(45) Date of Patent: *May 22, 2018

(54) BIOPSY SAMPLE STORAGE

(71) Applicant: Devicor Medical Products, Inc., Cincinnati, OH (US)

(72) Inventors: John A. Hibner, Mason, OH (US); Wells D. Haberstich, Loveland, OH (US); Kenneth E. Hogue, High Point, NC (US); Michele D'Arcangelo, Rome (IT); Trevor W. V. Speeg, Williamsburg, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/285,040

(22) Filed: Oct. 4, 2016

(65) Prior Publication Data

US 2017/0020492 A1    Jan. 26, 2017

Related U.S. Application Data

(63) Continuation of application No. 15/011,710, filed on Feb. 1, 2016, now Pat. No. 9,486,184, which is a (Continued)

(51) Int. Cl.
*A61B 5/00* (2006.01)
*A61B 10/02* (2006.01)
*A61B 10/00* (2006.01)

(52) U.S. Cl.
CPC ...... *A61B 10/0266* (2013.01); *A61B 10/0096* (2013.01); *A61B 10/0275* (2013.01);
(Continued)

(58) Field of Classification Search
CPC ... A61B 10/0275; A61B 10/0233; A61B 1/05; A61B 2010/045; A61B 2090/374; A61B 10/0266; A61B 10/0283; A61B 10/06
(Continued)

(56) References Cited

U.S. PATENT DOCUMENTS 2,853,071 A    9/1958  Saffir
5,213,110 A    5/1993  Kedem et al.
(Continued)

FOREIGN PATENT DOCUMENTS

AU    2007242954 A1    7/2008
AU    2013205330 B2    9/2014
(Continued)

OTHER PUBLICATIONS

Australian Patent Examination Report No. 1 dated May 28, 2012 for Application No. 2007242954, 2 pages.
(Continued)

*Primary Examiner* — May Abouelela
(74) *Attorney, Agent, or Firm* — Frost Brown Todd LLC

(57) ABSTRACT

A biopsy device may be used to obtain and store multiple tissue samples. The device permits the tissue samples to be stored in a sequenced fashion within a generally transparent tissue storage chamber disposed at a proximal end of the biopsy device. The tissue samples can be stored on flexible tissue sample strips arranged around the circumference of a rotating vacuum manifold disposed within the chamber.

20 Claims, 15 Drawing Sheets

Related U.S. Application Data continuation of application No. 13/347,941, filed on Jan. 11, 2012, now Pat. No. 9,462,999, which is a continuation of application No. 11/952,405, filed on Dec. 7, 2007, now Pat. No. 8,118,755.

(60) Provisional application No. 60/874,792, filed on Dec. 13, 2006, provisional application No. 60/869,736, filed on Dec. 13, 2006.

(52) U.S. Cl.
CPC .. *A61B 10/0283* (2013.01); *A61B 2010/0208* (2013.01); *A61B 2010/0225* (2013.01)

(58) Field of Classification Search
USPC .................. 600/562, 564, 566, 567
See application file for complete search history.

(56) References Cited

U.S. PATENT DOCUMENTS

| | | | |
|---|---|---|---|
| 5,526,822 A * | 6/1996 | Burbank ............ | A61B 10/0266 600/567 |
| 5,649,547 A | 7/1997 | Ritchart et al. | |
| 5,769,086 A | 6/1998 | Ritchart et al. | |
| 5,775,333 A | 7/1998 | Burbank et al. | |
| 5,928,164 A * | 7/1999 | Burbank ............ | A61B 10/0266 600/567 |
| 5,964,716 A | 10/1999 | Gregoire et al. | |
| 5,980,469 A | 11/1999 | Burbank et al. | |
| 6,007,497 A | 12/1999 | Huitema | |
| 6,017,316 A | 1/2000 | Ritchart et al. | |
| 6,077,230 A | 6/2000 | Gregoire et al. | |
| 6,086,544 A | 7/2000 | Hibner et al. | |
| 6,120,462 A | 9/2000 | Hibner et al. | |
| 6,142,956 A | 11/2000 | Kortenbach et al. | |
| 6,228,055 B1 | 5/2001 | Foerster et al. | |
| 6,231,522 B1 | 5/2001 | Voegele et al. | |
| 6,273,862 B1 * | 8/2001 | Privitera ............ | A61B 10/0275 600/568 |
| 6,409,970 B1 | 6/2002 | Phifer | |
| 6,428,487 B1 * | 8/2002 | Burdorff ............ | A61B 10/0275 600/568 |
| 6,485,436 B1 | 11/2002 | Truckai | |
| 6,544,194 B1 | 4/2003 | Kortenbach et al. | |
| 6,551,253 B2 | 4/2003 | Worm et al. | |
| 6,602,203 B2 | 8/2003 | Stephens et al. | |
| 6,659,338 B1 * | 12/2003 | Dittmann ............ | A01K 11/003 235/375 |
| 6,832,990 B2 | 12/2004 | Kortenbach et al. | |
| 6,875,182 B2 | 4/2005 | Wardle et al. | |
| 6,923,809 B2 | 8/2005 | Eggers et al. | |
| 6,986,748 B2 | 1/2006 | McAlister et al. | |
| 7,156,815 B2 | 1/2007 | Leigh et al. | |
| 7,204,811 B2 | 4/2007 | Kortenbach et al. | |
| 7,276,032 B2 | 10/2007 | Hibner | |
| 7,419,472 B2 | 9/2008 | Hibner et al. | |
| 7,556,622 B2 * | 7/2009 | Mark ................ | A61B 10/0275 210/348 |
| 7,641,668 B2 | 1/2010 | Perry et al. | |
| 7,645,240 B2 | 1/2010 | Thompson et al. | |
| 7,740,596 B2 | 6/2010 | Hibner | |
| 7,740,597 B2 | 6/2010 | Cicenas et al. | |
| 7,828,745 B2 | 11/2010 | McAlister et al. | |
| 7,828,748 B2 | 11/2010 | Hibner | |
| 7,846,107 B2 | 12/2010 | Hoffman et al. | |
| 7,854,707 B2 | 12/2010 | Hibner | |
| 7,858,038 B2 * | 12/2010 | Andreyko .......... | A61B 10/0096 422/512 |
| 7,867,173 B2 | 1/2011 | Hibner et al. | |
| 7,896,817 B2 * | 3/2011 | Garrison ............ | A61B 10/0275 600/562 |
| 7,918,804 B2 | 4/2011 | Monson et al. | |
| 7,985,239 B2 | 7/2011 | Suzuki | |
| 8,016,844 B2 | 9/2011 | Privitera et al. | |
| 8,118,755 B2 | 2/2012 | Hibner et al. | |
| 8,241,226 B2 | 8/2012 | Hibner et al. | |
| 8,485,987 B2 | 7/2013 | Videbaek et al. | |
| 9,039,634 B2 | 5/2015 | Speeg et al. | |
| 9,462,999 B2 | 10/2016 | Hibner et al. | |
| 2001/0047183 A1 * | 11/2001 | Privitera ............ | A61B 10/0275 606/170 |
| 2002/0077565 A1 * | 6/2002 | Burdorff ............ | A61B 10/0275 600/566 |
| 2003/0199753 A1 | 10/2003 | Hibner et al. | |
| 2004/0068291 A1 * | 4/2004 | Suzuki ............... | A61B 10/0096 606/205 |
| 2005/0038355 A1 * | 2/2005 | Gellman ............ | A61B 10/0275 600/564 |
| 2005/0215921 A1 * | 9/2005 | Hibner ............... | A61B 10/0266 600/566 |
| 2005/0277829 A1 * | 12/2005 | Tsonton ............. | A61B 5/055 600/423 |
| 2006/0258955 A1 * | 11/2006 | Hoffman ............ | A61B 10/06 600/564 |
| 2006/0282012 A1 * | 12/2006 | McAlister .......... | A61B 10/0266 600/565 |
| 2008/0004545 A1 * | 1/2008 | Garrison ............ | A61B 10/0275 600/566 |
| 2008/0082021 A1 | 4/2008 | Ichikawa et al. | |
| 2008/0214955 A1 | 9/2008 | Speeg et al. | |
| 2010/0106053 A1 * | 4/2010 | Videbaek .......... | A61B 10/0096 600/564 |
| 2012/0116246 A1 | 5/2012 | Hibner et al. | |
| 2016/0143632 A1 | 5/2016 | Hibner et al. | |

FOREIGN PATENT DOCUMENTS

| | | |
|---|---|---|
| CN | 101301213 A | 11/2008 |
| CN | 102217954 A | 10/2011 |
| EP | 1642534 A2 | 4/2006 |
| EP | 1932482 A1 | 6/2008 |
| JP | H09-510638 | 10/1997 |
| JP | H11-009605 | 1/1999 |
| JP | 2000-279418 | 10/2000 |
| JP | 2000-516832 A | 12/2000 |
| JP | 2002-530139 A | 9/2002 |
| JP | 2005-199044 | 7/2005 |
| JP | 2006-095314 A | 4/2006 |
| JP | 2009-505697 | 2/2009 |
| JP | 51-12035 B2 | 1/2013 |
| JP | 55-79813 B2 | 8/2014 |
| JP | 59-18313 B2 | 5/2016 |
| WO | WO 98/33436 | 8/1998 |
| WO | WO 00/30531 | 6/2000 |
| WO | WO 2004/016177 | 2/2004 |
| WO | WO 2006/005344 | 1/2006 |
| WO | WO 2006/124489 | 11/2006 |
| WO | WO 2007/112751 | 10/2007 |

OTHER PUBLICATIONS

Australian Patent Examination Report No. 2 dated Dec. 21, 2012 for Application No. 2007242954, 4 pages.
Australian Patent Examination Report No. 3 dated Jun. 19, 2013 for Application No. 2007242954, 3 pages.
Australian Patent Examination Report No. 4 dated Jul. 25, 2013 for Application No. 2007242954, 4 pages.
Australian Patent Examination Report No. 1 dated Jun. 7, 2013 for Application No. 2013205330, 4 pages.
Australian Patent Examination Report No. 2 dated Oct. 23, 2013 for Application No. 2013205330, 3 pages.
Canadian Office Action dated Oct. 31, 2014 for Application No. 2,614,259, 5 pages.
Canadian Office Action dated Nov. 24, 2015 for Application No. 2,614,259, 4 pages.
Chinese Office Action dated Aug. 6, 2010 for Application No. 200710186190.0, 3 pages.
Chinese Office Action dated May 9, 2012 for Application No. 201110077184.8, 7 pages.

(56) References Cited

OTHER PUBLICATIONS

Chinese Office Action dated Feb. 20, 2013 for Application No. 201110077184.8, 8 pages.
European Communication dated Apr. 29, 2008 for Application No. 07254808.4, 6 pages.
European Communication dated Jun. 4, 2009 for Application No. 07254808.4, 3 pages.
Indian Office Action dated Apr. 29, 2016 for Application No. 1673/KOL/2007, 2 pgs.
International Search Report and Written Opinion dated Nov. 4, 2008 for Application No. PCT/US2007/87075.
Japanese Office Action dated Dec. 11, 2013 for Application No. 2012-224799, 2 pages.
Japanese Office Action dated Jul. 7, 2015 for Application No. JP 2014-143061, 3 pgs.
Japanese Office Action dated Jul. 9, 2015 for Application No. 2014-143061, 5 pages.
U.S. Appl. No. 60/867,736, filed Dec. 13, 2006.
U.S. Appl. No. 60/874,792, filed Dec. 13, 2006.
Canadian Office Action dated Nov. 24, 2016 for Application No. 2,614,259, 4 pages.
Japanese Office Action dated Apr. 4, 2017 for Application No. 2016-077112, 3 pages.
Canadian Office Action dated Jan. 12, 2018 for Application No. 2,614,259, 4 pages.
Japanese Office Action dated Nov. 30, 2017 for Application No. 2016-077112, 4 pages.

* cited by examiner

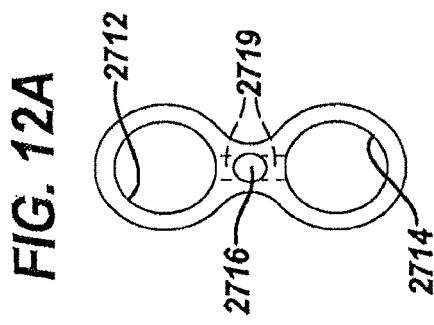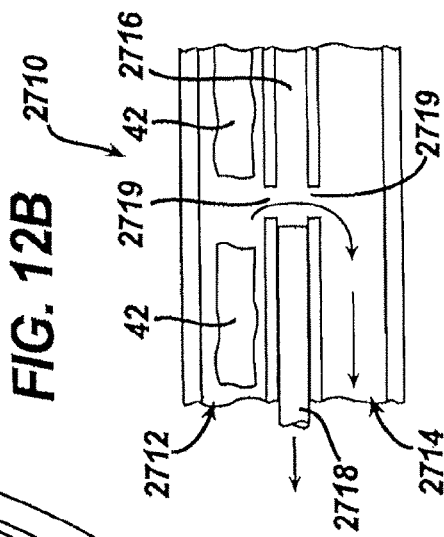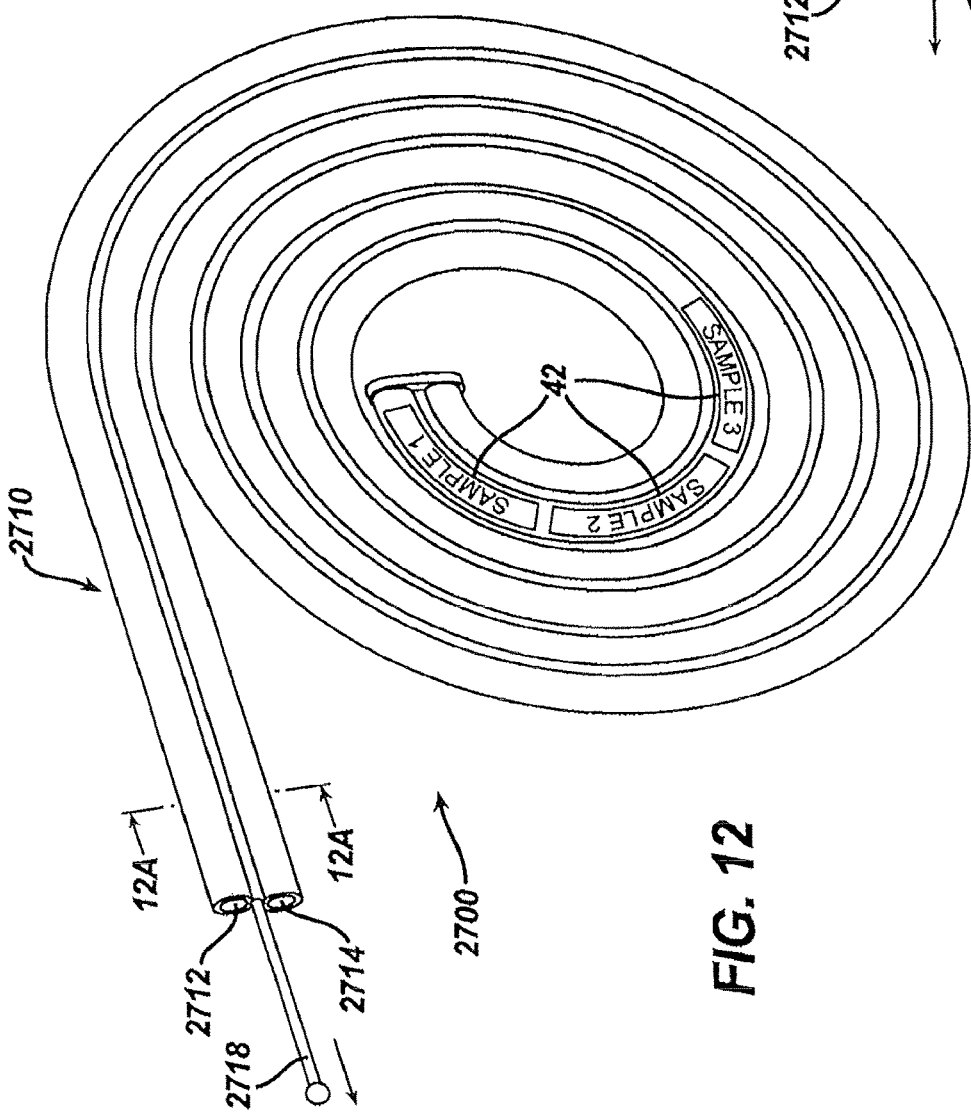

FIG. 16

| Action | "Sample" Button (170) | "Clear Probe" Button (172) | "Aspirate/Insert" Button (174) | Aperture (114) | Lateral Lumen (108) | Master Control Valve (4060) Position | Saline/Vacuum Valve (4080) Position |
|---|---|---|---|---|---|---|---|
| Ready State | — | — | — | closed | sealed/dead-headed | up | up |
| Sample | press & release or press & hold | — | — | open | vacuum | down | down |
| Clear Probe | — | press & release or press & hold | — | closed | vent | middle | up |
| | | | | closed | saline | down | up |
| Insert Pain or Bleeding Medication or Apply Marker, etc. | — | — | press & release | open | vent | middle | down |
| Aspirate Cavity | — | — | press & hold | open | vacuum | down | down |

BIOPSY SAMPLE STORAGE

PRIORITY

This application is a continuation of U.S. patent application Ser. No. 15/011,710, filed Feb. 1, 2016, published as U.S. patent publication number 2016/0143632 on May 26, 2016; which is a continuation of U.S. patent application Ser. No. 13/347,941, filed Jan. 11, 2012, issued as U.S. Pat. No. 9,462,999 on Oct. 11, 2016; which is a continuation of and incorporates by reference U.S. patent application Ser. No. 11/952,405, filed Dec. 7, 2007, issued as U.S. Pat. No. 8,118,755 on Feb. 21, 2012; which claims priority to and incorporates by reference U.S. provisional application Ser. No. 60/869,736, filed Dec. 13, 2006, and U.S. provisional application Ser. No. 60/874,792, filed Dec. 13, 2006.

BACKGROUND

Some embodiments of the present invention relate in general to biopsy devices, and more particularly to biopsy devices having the capability to store multiple tissue samples, such as in a spaced-apart, sequenced manner, within a portion of the biopsy device.

When a suspicious tissue mass is discovered in a patient's breast or in another area through examination, ultrasound, MRI, X-ray imaging or the like, it may be necessary to perform a biopsy procedure to remove one or more samples of that tissue in order to determine whether the mass contains cancerous cells. A biopsy may be performed using an open or percutaneous method. Medical devices for obtaining tissue samples for subsequent sampling and/or testing are known in the biopsy art. For instance, a biopsy instrument now marketed under the tradename MAMMOTOME is commercially available from Ethicon Endo-Surgery, Inc. for use in obtaining breast biopsy samples.

An open biopsy may be performed by making a large incision in the breast and removing either the entire mass, called an excisional biopsy, or a substantial portion of it, known as an incisional biopsy. An open biopsy is a surgical procedure that may be done as an outpatient procedure in a hospital or a surgical center, and may involve a high cost and a high level of trauma to the patient. Open biopsy may carry relatively higher risk of infection and bleeding than does percutaneous biopsy, and the disfigurement that may result from an open biopsy may make it difficult to read future mammograms. Further, the aesthetic considerations of the patient might make open biopsy even less appealing due to the potential risk of disfigurement. Given that some biopsies show that the suspicious tissue mass is not cancerous, the potential downsides of the open biopsy procedure might render this method inappropriate in some cases.

Percutaneous biopsy may be less invasive than open biopsy. Percutaneous biopsy may be performed using fine needle aspiration (FNA), core needle biopsy, or otherwise. In FNA, a very thin needle may be used to withdraw fluid and cells from the suspicious tissue mass. This method may be low-pain, so low-pain that local anesthetic is not necessarily always used because the application of it may be more painful than the FNA itself. However, in some FNA procedures, only a small number of cells might be obtained through the procedure, rendering it relatively less useful in some situations in analyzing the suspicious tissue and making an assessment of the progression of the cancer less simple if the sample is found to be malignant.

During some core needle biopsy procedures, a small tissue sample may be removed allowing for a pathological assessment of the tissue, including an assessment of the progression of any cancerous cells that are found.

The biopsy instrument marketed under the trade name MAMMOTOME is commercially available from ETHICON ENDO-SURGERY, INC. generally retrieves multiple core biopsy samples from one insertion into breast tissue with vacuum assistance. In particular, a cutter tube is extended into a probe to cut tissue prolapsed into a side aperture under vacuum assistance, and then the cutter tube is fully retracted between cuts to extract the sample.

With a device having a relatively long cutter travel, the rate of sample taking may be limited not only by the time required to rotate or reposition the probe but also by the time needed to translate the cutter. As an alternative to relatively "long stroke" biopsy devices, a "short stroke" biopsy device is described in the following commonly assigned patent applications: U.S. patent application Ser. No. 10/676,944, entitled "Biopsy Instrument with Internal Specimen Collection Mechanism," filed Sep. 30, 2003 in the name of Hibner et al., published as U.S. Pub. No. 2005/0215921; and U.S. patent application Ser. No. 10/732,843, entitled "Biopsy Device with Sample Tube," filed Dec. 10, 2003 in the name of Cicenas et al, published as U.S. Pub. No. 2004/0153003, both of which are incorporated herein by reference. The cutter can be cycled through a distance substantially equal to or slightly greater than the distance across the side aperture, reducing the sample time.

The following patent documents disclose various biopsy devices, and are incorporated herein by reference in their entirety: U.S. Pat. No. 6,273,862 issued Aug. 14, 2001; U.S. Pat. No. 6,231,522 issued May 15, 2001; U.S. Pat. No. 6,228,055 issued May 8, 2001; U.S. Pat. No. 6,120,462 issued Sep. 19, 2000; U.S. Pat. No. 6,086,544 issued Jul. 11, 2000; U.S. Pat. No. 6,077,230 issued Jun. 20, 2000; U.S. Pat. No. 6,017,316 issued Jan. 25, 2000; U.S. Pat. No. 6,007,497 issued Dec. 28, 1999; U.S. Pat. No. 5,980,469 issued Nov. 9, 1999; U.S. Pat. No. 5,964,716 issued Oct. 12, 1999; U.S. Pat. No. 5,928,164 issued Jul. 27, 1999; U.S. Pat. No. 5,775,333 issued Jul. 7, 1998; U.S. Pat. No. 5,769,086 issued Jun. 23, 1998; U.S. Pat. No. 5,649,547 issued Jul. 22, 1997; U.S. Pat. No. 5,526,822 issued Jun. 18, 1996; and US Patent Application 2003/0199753 published Oct. 23, 2003 to Hibner et al. U.S. Pat. No. 5,526,822, incorporated by reference above, discloses a tissue sample cassette, including a rotary sample cassette that is belt driven. Other tissue sample storage devices are disclosed in U.S. patent application Ser. No. 10/953,395, entitled "Biopsy Device with Sample Storage," filed Sep. 29, 2004, published as U.S. Pub. No. 2006/0074343; and U.S. patent application Ser. No. 11/198,558 filed Aug. 8, 2005, entitled "Biopsy Device with Replaceable Probe and Incorporating Vibration Insertion Assist and Static Vacuum Source Sample Stacking Retrieval," published as U.S. Pub. No. 2007/0032741, each of which is incorporated by reference herein.

While a variety of biopsy devices have been made and used, and a variety of tissue sample storage devices and techniques have been devised, it is believed that no one prior to the inventors has made or used a biopsy system as described in the appended claims.

BRIEF DESCRIPTION OF THE DRAWINGS

While the specification concludes with claims particularly pointing out and distinctly claiming the present invention, it is believed the same will be better understood by reference to the following description, taken in conjunction with the accompanying drawings in which:

FIG. 2A is a schematic cross-section taken along section 2A-2A in FIG. 2.

FIG. 12 illustrates a tissue holder for holding tissue samples in an end-to-end configuration.

FIG. 12A is a cross-sectional schematic illustration taken along lines 12A-12A in FIG. 12.

FIG. 12B is a sectional view taken along a portion of the length of the tissue holder shown in FIG. 12.

FIG. 16 illustrates multiple control states that can be employed in controlling a biopsy device.

DETAILED DESCRIPTION

Figure 1:
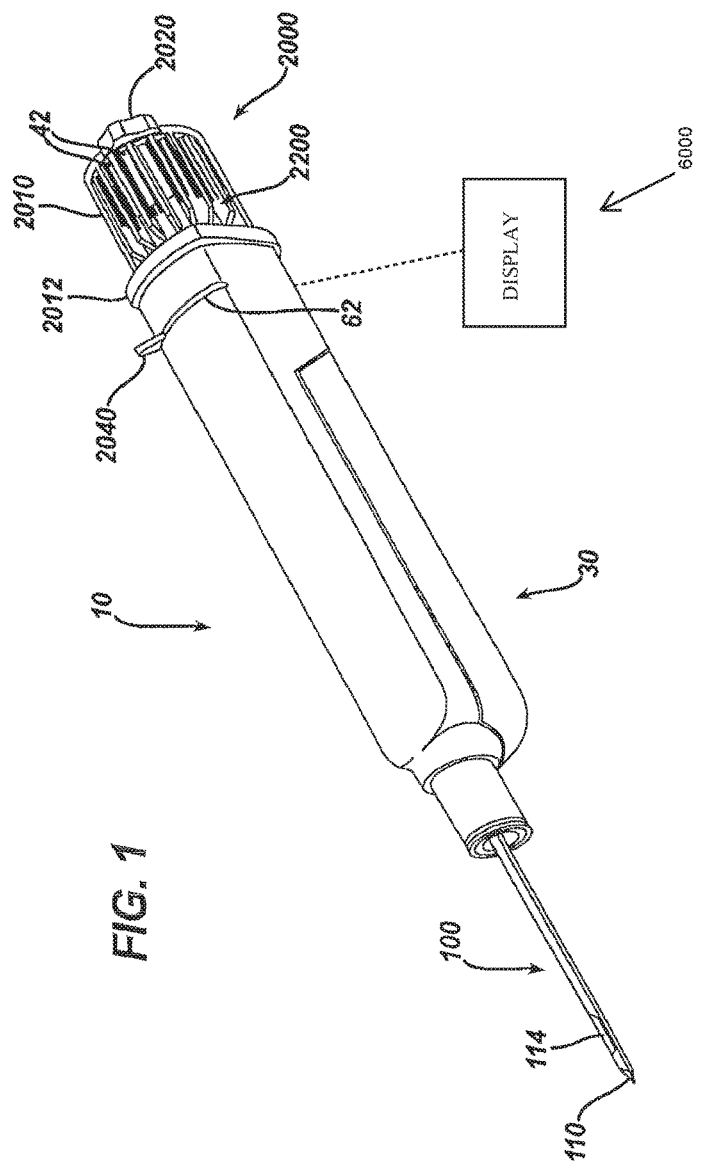
FIG. 1 is a schematic illustration of a biopsy device having a tissue sample storage assembly according to one embodiment of the present invention.

FIG. 1 shows a biopsy device 10 according to one embodiment of the present invention. The biopsy device 10 of this example comprises a handpiece identified generally as numeral 30. Handpiece 30 can be held comfortably in a single hand, and can be manipulated with a single hand.

Biopsy device 10 can include a tissue piercing portion, such as cannula 100, extending distally from the handpiece 30. The cannula 100 can include a distal tissue piercing tip 110 and a transverse tissue receiving aperture 114 spaced proximally of the tip 110. The cannula 100 can be inserted into a tissue mass to be sampled. Tissue drawn into the aperture 114 can then be severed by the distal end 122 of a tubular cutter 120 (FIG. 2) translating within the cannula 100.

The biopsy device 10 of the present example also includes a tissue storage assembly 2000, which can be disposed at a proximal end of the handpiece 30, proximal to the cutter 120. The tissue storage assembly 2000 can include a generally transparent cover 2010, which can be releasably joined to biopsy device 10, such as at the proximal end of the handpiece 30. Of course, the cover 2010 may be substantially translucent, opaque, combinations of transparent and opaque, etc., or have any other suitable properties. The cover 2010 can be releasably joined to the proximal end of the handpiece 30 by any suitable attachment mechanism or feature, including but not limited to by snap fit, bayonet fitting, threaded style fitting, etc. In FIG. 1, the cover 2010 has a flange 2012 that provides a releasable snap fit engagement with proximal end of handpiece 30.

The tissue storage assembly 2000 shown also includes at least one tissue holder 2200 disposed within a removable cover 2010, the holder 2200 being releasably carried on a rotatable member. In the present example, the rotatable member is in the form of a manifold 2300 (FIG. 7), though other structures or configurations may be used. The manifold 2300 can be disposed at least partially within the cover 2010. The tissue sample holder 2200 can be shaped or otherwise configured to hold a plurality of tissue samples (designated generally by numeral 42), such as those severed by the cutter 120, in a sequenced, spaced apart order on the holder 2200.

The rotatable manifold 2300 and the tissue holder 2200 of the present example can be rotated automatically, such as by being rotationally indexed through a predetermined angular increment each time a tissue sample 42 is severed, as described below. A manual rotation knob 2020 can be provided to permit manual rotation of the manifold 2300 and the tissue holder 2200, in case the user desires to "override" the automatic indexing. The tissue storage assembly 2000 can also include an actuator, such as a control lever 2040 for selecting the direction of rotational indexing (clockwise or counterclockwise) of the rotatable manifold 2300 and the tissue holder 2200 within the transparent cover 2010. Of course, as with other components described herein, knob 2020 and lever 2040, are merely optional, and may be modified, substituted, supplemented, or omitted as desired.

Figure 6:
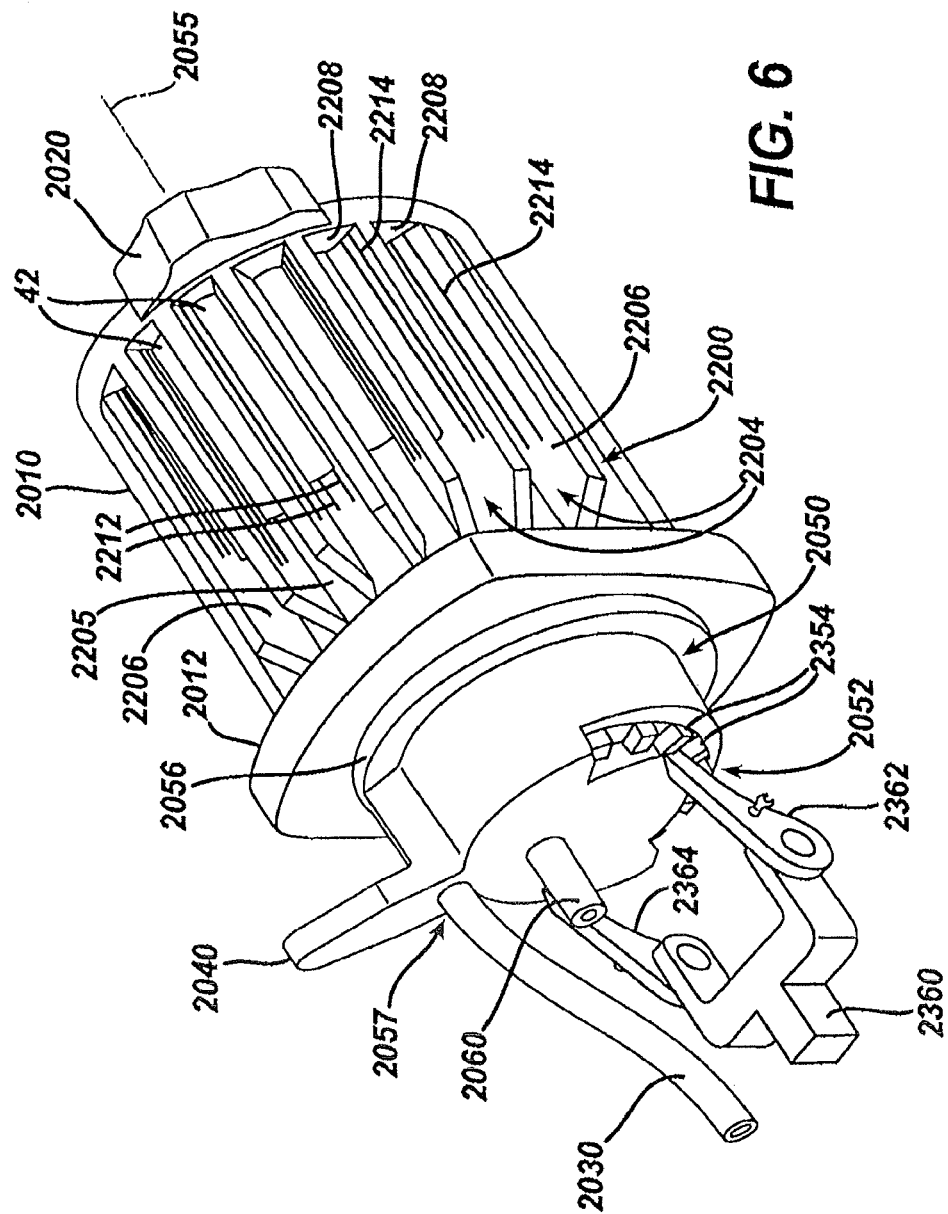
FIG. 6 provides an enlarged illustration of an exemplary tissue storage assembly.
Figure 7:
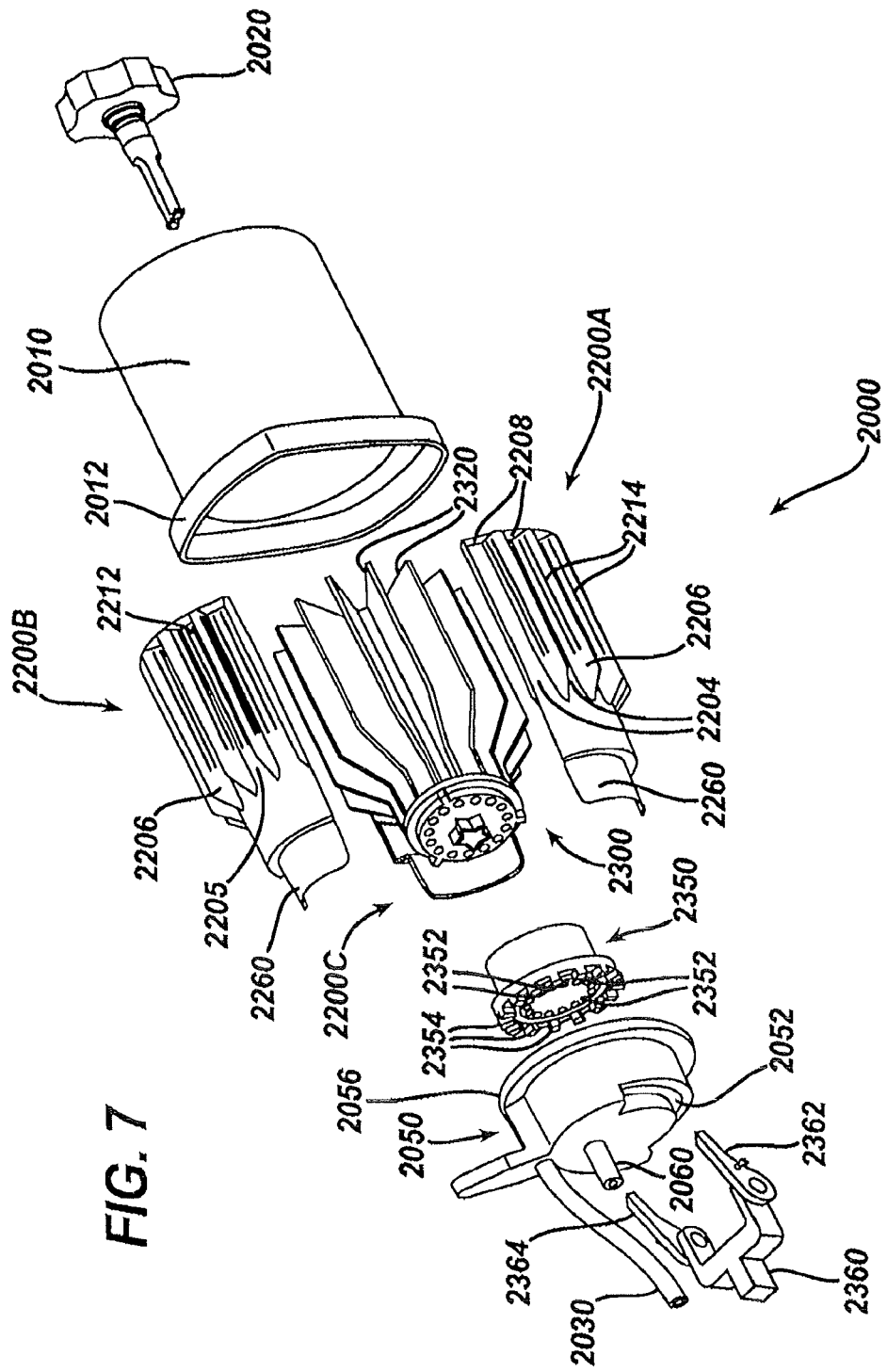
FIG. 7 provides an exploded view of components of the tissue storage assembly of FIG. 6.
Figure 8:
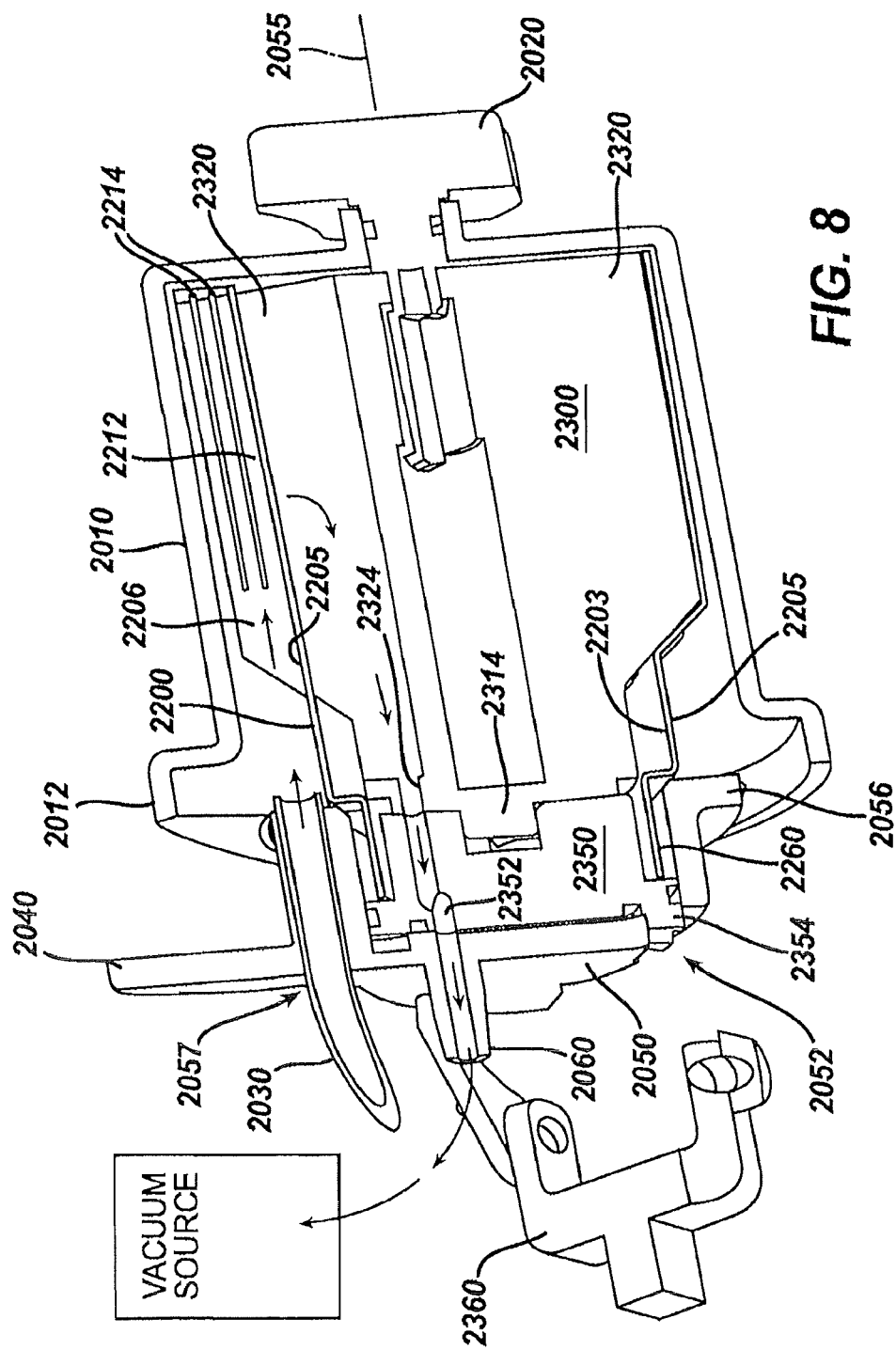
FIG. 8 provides a cross-sectional illustration of components of the tissue storage assembly of FIG. 6.

A sequence of operation of a biopsy device employing a tissue storage assembly 2000 according to one embodiment of the present invention is shown in FIGS. 2-5. In FIGS. 2-5, the tissue storage assembly 2000 is shown with the cover 2010 removed. FIGS. 6, 7, and 8 illustrate the tissue storage assembly 2000 of the present example in more detail.

Figure 2:
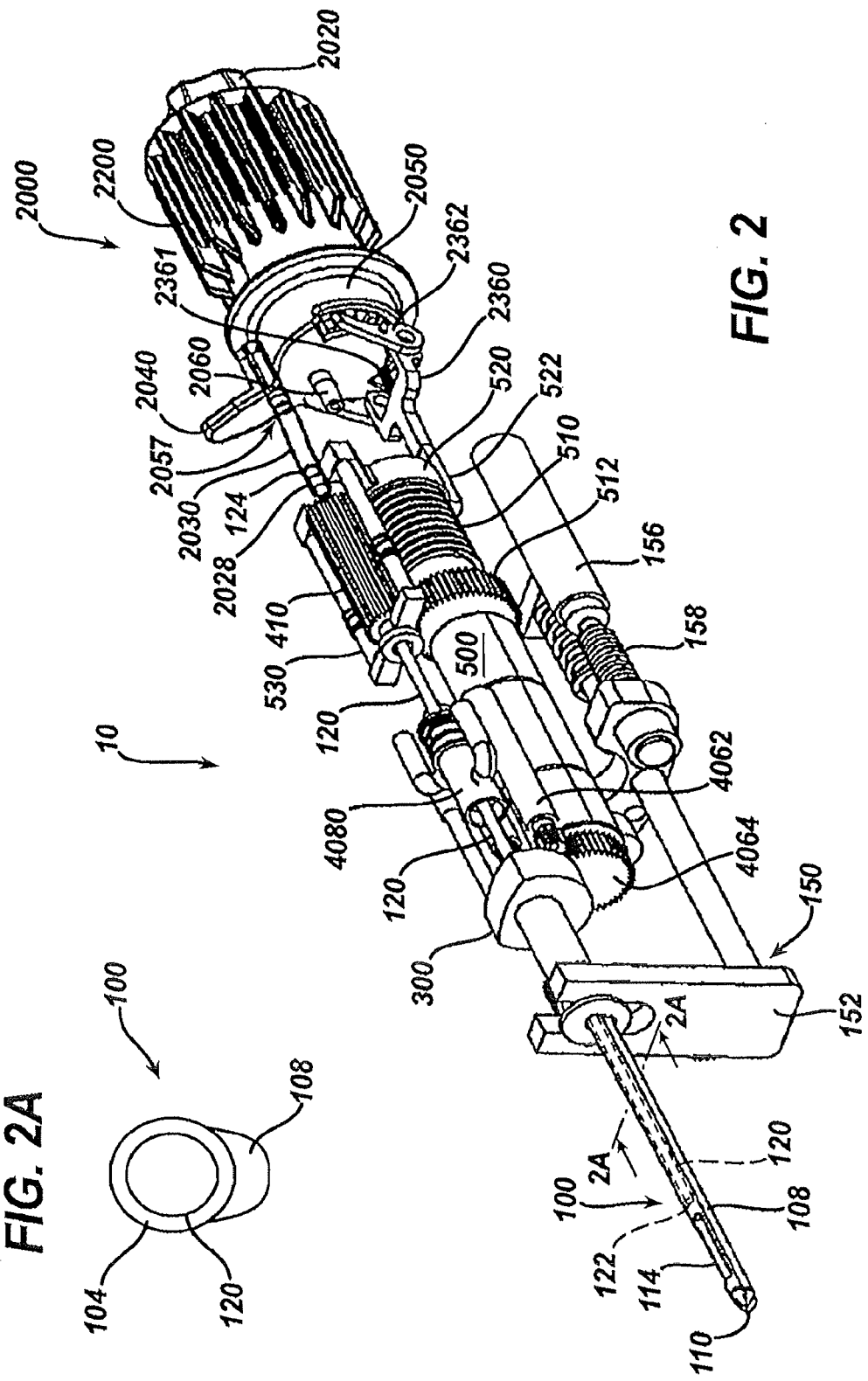
FIG. 2 is a schematic illustration of a biopsy device having a tissue sample storage assembly according to one embodiment of the present invention, with portions of the biopsy device removed to illustrate internal components of the device, and with the cutter in a retracted position.

Referring to FIG. 2, the internal components of an exemplary biopsy device 10 suitable for use in a stereotactic application are shown. In FIG. 2, the cannula 100 is shown in a "fired" position, corresponding to the cannula 100 having been directed into tissue by a firing assembly 150. The firing assembly 150 of the present example includes a firing fork 152, which can be cocked (such as by a manual cocking apparatus or by a cocking motor 156), with the energy for firing being stored in a firing spring 158. Alternatively, firing assembly 150 may have any other suitable configuration or may be omitted altogether.

A tubular cutter 120 is disposed in a cutter lumen 104 of cannula 100 in the present example. In FIG. 2, the cutter 120 is shown in a retracted position, with a distal cutting end 122 (shown in phantom) of the cutter 120 positioned just proximal of the tissue receiving aperture 114 in cannula 100. After firing the cannula 100 into tissue, the cutter 120 retracts to the position shown in FIG. 2 in an exemplary mode of operation.

Referring to FIG. 2 and FIG. 2A, the cannula 100 can also include a vacuum lumen 108 disposed beneath cutter lumen 104. Vacuum lumen 108 of the present example communicates vacuum to cutter lumen 104 just below port aperture 114 through a plurality of passageways 107 (FIG. 13) to assist in drawing tissue into port 114 when the cannula 100 is disposed in tissue and the cutter 120 is in the retracted position shown in FIG. 2. The cutter 120 extends from the distal cutting end 122 to a cutter proximal end 124. Intermediate the distal cutting end 122 and the proximal end 124, the cutter 120 passes through the cutter lumen 104 of cannula 100, a vacuum manifold 300, saline/vacuum valve assembly 4080, and a cutter gear 410.

In the present example, the proximal end 124 of the cutter 120 communicates with a distal end of a tissue sample transfer tube 2030. Sample transfer tube 2030 can be a flexible tube joined to the proximal end 124 of cutter 120 by a slip joint 2028, or other suitable connection for permitting relative axial motion and rotation of the cutter end 124 relative to the tube 2030. The proximal end of the sample transfer tube 2030 communicates with a tissue sample port 2057 of proximal cover 2050 of the tissue storage assembly 2000. The proximal cover 2050 encloses the proximal end of the tissue storage assembly 2000. The proximal cover 2050 and the generally transparent cover 2010, together, provide a tissue storage chamber within which the manifold 2300 and the tissue holder 2200 are at least partially disposed. The port 2057 and a vacuum port 2060 for communicating vacuum to the manifold 2300 can be formed integral with the cover 2050. It will be appreciated in view of the teachings herein, however, that sample transfer tube 2030 may be varied, substituted, supplemented, or omitted as desired; and that a variety of other components or features may be used to provide fluid communication between cutter 120 and tissue storage assembly 2000.

Tissue samples 42 cut by cutter 120 can be transported through cutter 120, then through sample transfer tube 2030, to be deposited into the tissue storage chamber of the tissue storage assembly 2000. Vacuum can be provided from a vacuum source to the tissue storage assembly 2000 through vacuum port 2060 in cover 2050 or otherwise. The tissue samples 42 entering the tissue storage chamber through the port 2057 in cover 2050 are deposited on the tissue holder 2200 in the present example.

The proximal cover 2050 can also include an access opening 2052, as shown in FIG. 6. Teeth 2354 of a manifold rotation gear 2350 can be engaged by an indexing pawl 2362 through opening 2052. Manifold rotation gear 2350 can be coupled to the manifold 2300 by a spline connection or other suitable connection, such that rotation of gear 2350 causes manifold 2300 to rotate.

In the present example, the proximal cover 2050 includes a flange 2056 that can be captured between mating halves (not shown) of the body of the biopsy device 10, such that the cover 2050 can be rotated about a longitudinal axis 2055 (FIG. 6) of the tissue storage assembly 2000. Lever 2040 can be employed to rotate the cover 2050 (and access opening 2052) circumferentially from a first o'clock position to a second o'clock position. When lever 2040 is in the position shown in the Figures (e.g., FIGS. 1 and 6), pawl 2362 engages the teeth 2354 through opening 2052. When lever 2040 is repositioned to the other end of the slot 62 in the outer cover of the biopsy device (FIG. 1), the cover 2050 and access opening 2052 are rotated so that pawl 2364 engages the teeth 2354. Pawl 2362 provides indexed rotation of the manifold 2300 in one direction about axis 2055, while pawl 2364 provides indexed rotation of the manifold 2300 in the opposite direction about axis 2055.

By changing the position of lever 2040, the entry point of the tissue samples 42 into the tissue storage assembly 2000 is also changed in the present example. The position of port 2057 moves circumferentially when the position of lever 2040 is changed, with the transfer tube 2030 accommodating this motion. The entry point of the tissue samples is offset from a twelve o'clock position (straight up) in the embodiment shown. The lever 2040 can be employed to select the tissue entry point to be at either about a 2 o'clock or about a 10 o'clock position, so that the entry of the samples into the assembly 2000 can be seen through clear cover 2010 of the tissue storage assembly 2000 by an operator using the biopsy device 10 in a stereotactic environment, where the top of the biopsy device 10 may be positioned close to the surface of the underside of the stereotactic table.

It will be appreciated that any other suitable structure(s) or device(s) may be used in addition to or in lieu of lever 2040 to reposition port 2057. For instance, one or more motors or transmissions may be used to selectively reposition port 2057. Alternatively, the circumferential or angular position port 2057 may be substantially fixed (e.g., at 12 o'clock, etc.). Similarly, pawls 2362, 2364 may be varied, substituted, supplemented, or omitted as desired.

Referring again to FIG. 2, a cutter lead screw 510 is supported on the biopsy device 10, to be rotated by a cutter motor 500. Rotation of screw 510 causes cutter carriage nut 520 to advance or retract on screw 510, depending on the direction of rotation of the screw 510. Nut 520 can be attached to, or integral with, a cutter carriage 530. Cutter 120 is rotatably supported on the carriage 530 in this example, so that cutter 120 can be rotated by gear 410 as the cutter carriage translates the cutter 120. Movement of nut 520 on screw 510 causes carriage 530 and cutter 120 to move axially, either proximally (retract) or distally (advance), depending on the direction of rotation of motor 500 and screw 510. The cutter 120 is rotated about its axis by cutter rotation gear 410 as gear 410 engages drive gear 512. Rotation of drive gear 512 can also be powered by motor 500. Cutter 120 may thus be rotated and translated concomitantly by activation of motor 500. In FIG. 2, the cutter carriage nut 520 is shown in its proximal (retracted) position corresponding to distal end 122 of cutter 120 being positioned just proximal of the aperture 114.

Still referring to FIG. 2, pawl 2362 is pivotably mounted on pawl sled 2360. In FIG. 2, the pawl sled 2360 is shown in its proximal most position. The sled 2360 has been pushed proximally by a tab extension 522 on the carriage nut 520. Proximal movement of sled 2360 compresses sled spring 2361. The compressed sled spring 2361 can be employed to urge sled 2360 distally (advance sled) when nut 520 and tab extension 522 advance distally on the lead screw 510. Of course, spring 2361 may be omitted, varied, etc., if desired.

Figure 3:
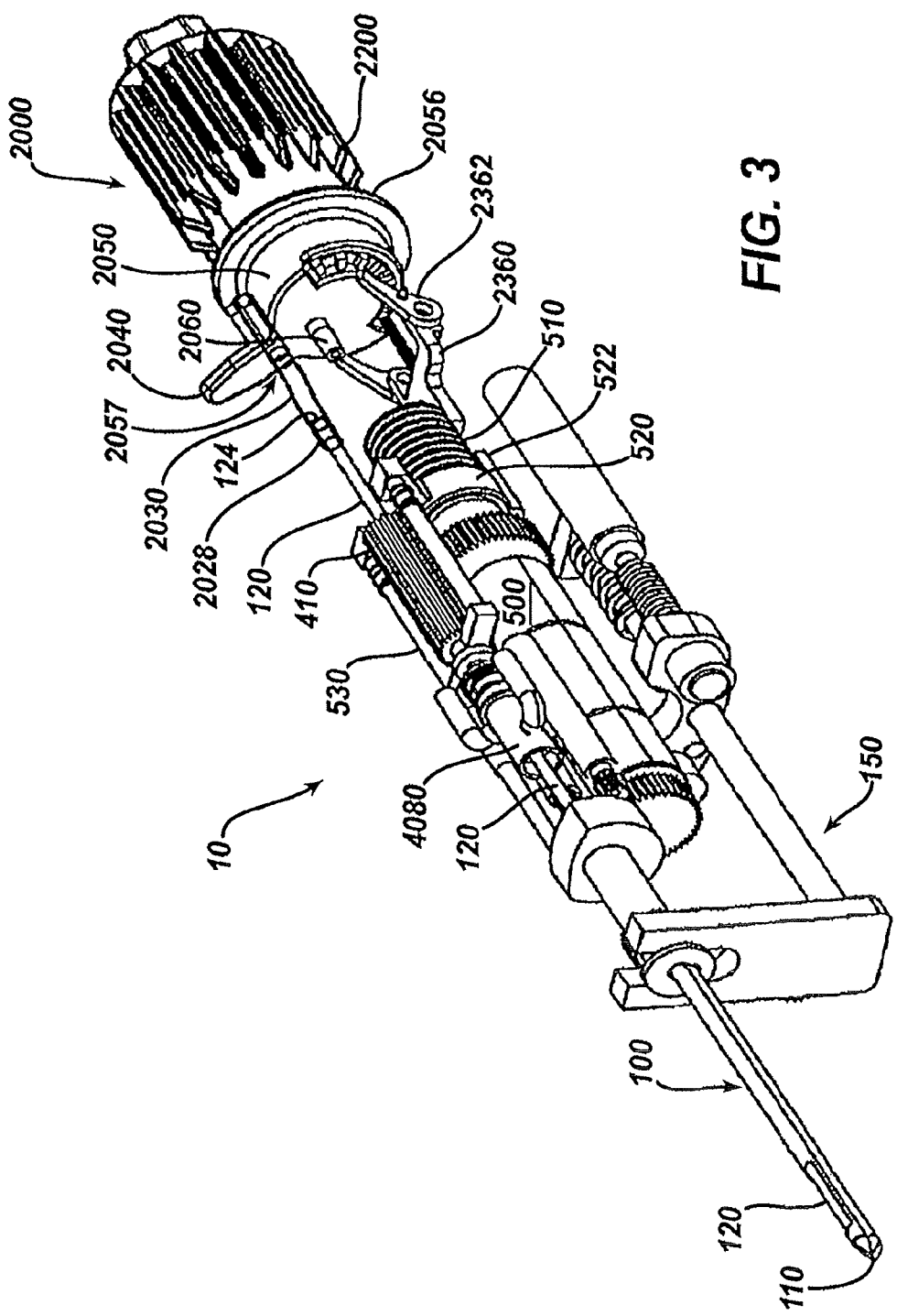
FIG. 3 is a schematic illustration of a biopsy device having a tissue sample storage assembly according to one embodiment of the present invention, with portions of the biopsy device removed to illustrate internal components of the device, with the cutter advanced across a tissue receiving port.

In the position shown in FIG. 2, the biopsy device 10 is ready to obtain a tissue sample 42. A vacuum control module 5000 (FIG. 15) can direct vacuum to the vacuum lumen 108 to draw tissue into the aperture 114. Referring to FIG. 3, the cutter 120 has been advanced to its distal most position to sever a tissue sample 42, and the cutter 120 is shown to extend across and closes the aperture 114 in cannula 100. As the cutter 120 advances from the position of FIG. 2 to the position shown in FIG. 3, the cutter 120 also rotates under the action of cutter rotation gear 410, which is rotated by drive gear 512. In FIG. 3, carriage 530 and cutter 120 have been advanced by translation of nut 520 on screw 510. As nut 520 moves distally, tab extension 522 also moves distally, and pawl sled 2360 is pushed distally by expansion of spring 2361. The pawl 2362 is disengaged and "rides over" teeth 2354 of the manifold gear 2350 as the cutter 120 advances distally from the position shown in FIG. 2 to the position shown in FIG. 3.

Figure 4:
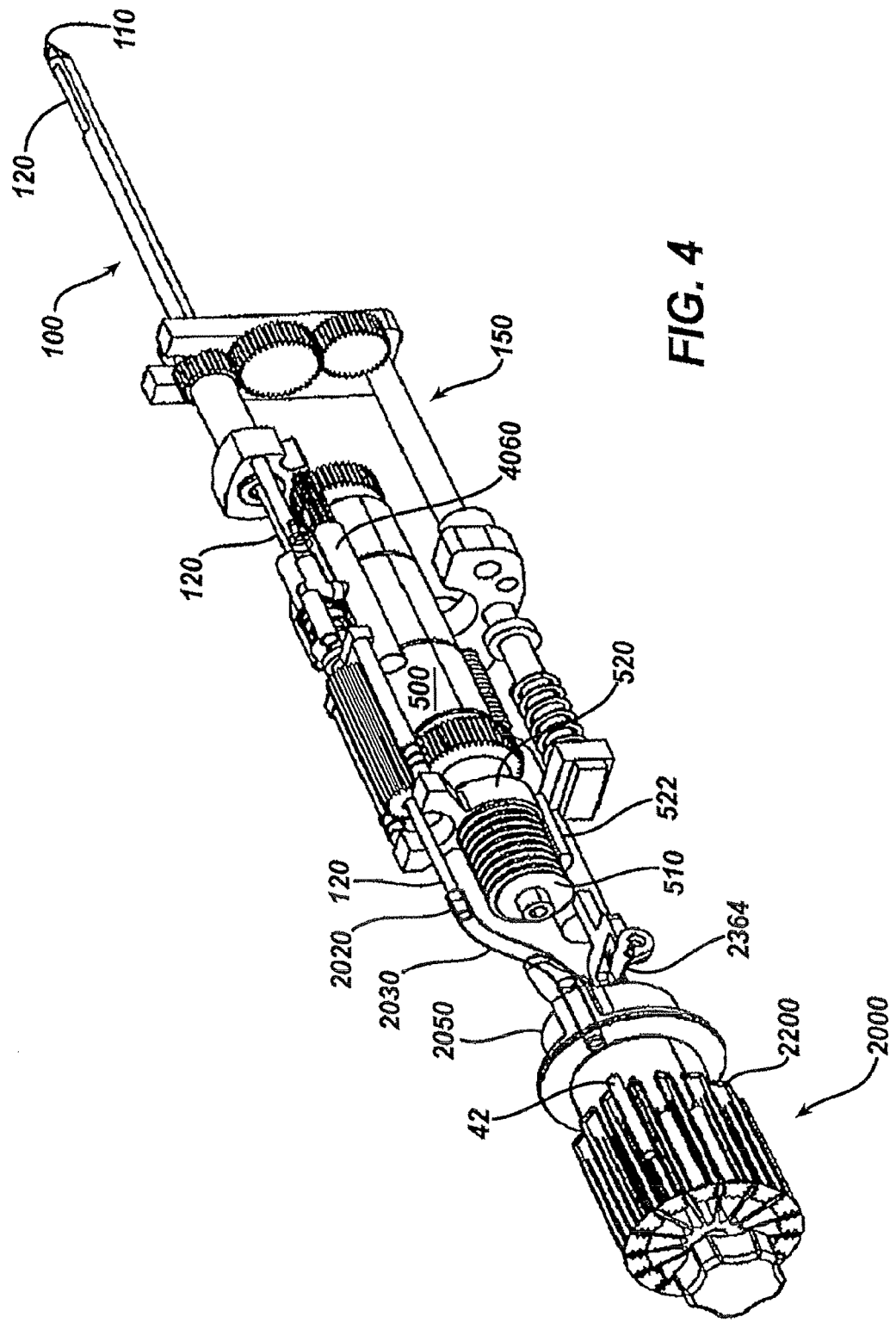
FIG. 4 is a schematic illustration of a biopsy device having a tissue sample storage assembly according to one embodiment of the present invention, with portions of the biopsy device removed to illustrate internal components of the device, and showing a tissue sample being deposited on the tissue sample holder.

Referring to FIG. 4, a severed tissue sample 42 is shown exiting the sample transfer tube 2030 and being deposited on the tissue holder 2200. To provide transfer of the severed tissue sample 42 from the cannula 100 to the tissue storage assembly 2000, the vacuum in vacuum lumen 108 is turned off and a vacuum control valve is employed to provide atmospheric pressure to the vacuum lumen 108, while cutter 120 is still in its distal most position covering the tissue receiving aperture 114. Additionally, or alternatively, a supply of saline can be provided. Valving can be employed to direct the saline to flow distally through the vacuum lumen 108 of cannula 100 to one or more holes or passageways 107 providing fluid communication between cutter lumen 104 and vacuum lumen 108 at the distal end of cannula 100. The saline flow and/or the atmospheric pressure provide a proximally directed force on the tissue sample severed by cutter 120, which provides a proximally directed "push" on the severed tissue sample disposed at the distal portion of cutter 120.

Additionally, a tissue storage vacuum source can be provided that communicates a vacuum to the vacuum port 2060. The vacuum provided at port 2060 is communicated through tissue storage assembly 2000 to the cutter 120 via sample transfer tube 2030. Accordingly, the vacuum provided at port 2060 provides a proximally directed "pull" on the severed tissue sample in the cutter 120. The combined proximally directed "push" and "pull" on the severed tissue sample serve to convey the tissue sample 42 through the cutter 120 (from the cutter distal end 122 to the cutter proximal end 124), through the sample transfer tube 2030, (which can extend through an opening in cover 2050 as shown in FIG. 8), and into the tissue storage assembly 2000, to be deposited on a portion of the tissue holder 2200 (such as a recess or compartment) aligned with the sample transfer tube 2030. Tissue sample 42 is shown being deposited on the tissue holder 2200 in FIG. 4. The vacuum provided to vacuum port 2060 can be kept "on" throughout the sample cutting cycle, so that vacuum pressure is present inside the hollow cutter 120 at all times. Alternatively, the vacuum provided to vacuum port 2060 can be cycled on and off according to a predetermined schedule. Other ways in which a tissue sample 42 may be conveyed from the cutter distal end 122 to the tissue holder 2200, including structures and devices that may be used, as well as fluid communication parameters, will be apparent to those of ordinary skill in the art in view of the teachings herein.

Figure 5:
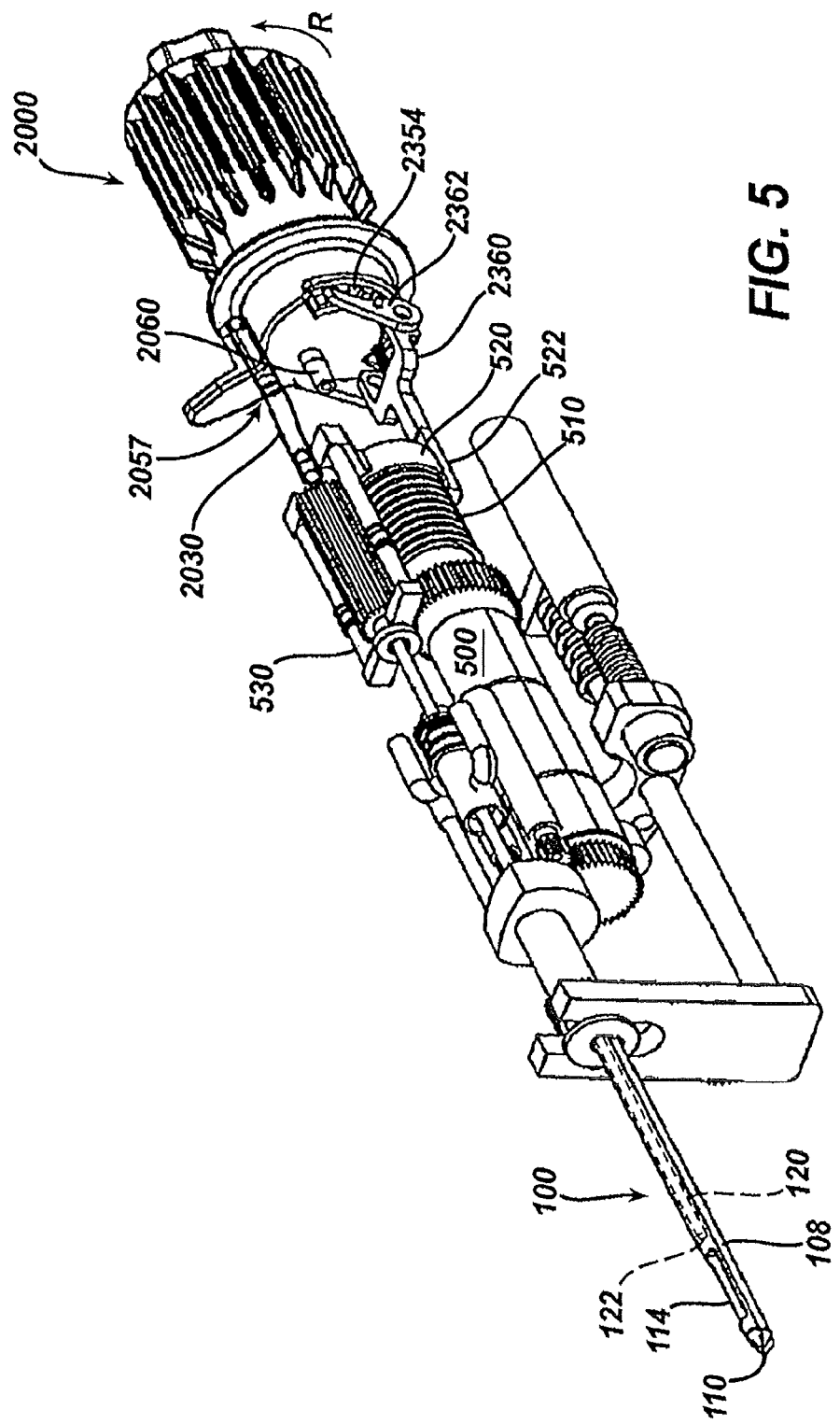
FIG. 5 is a schematic illustration of a biopsy device having a tissue sample storage assembly according to one embodiment of the present invention, with portions of the biopsy device removed to illustrate internal components of the device, and showing retraction of the cutter and indexing of the tissue sample holder.

Referring to FIG. 5, the manifold and 2300 and the tissue holder 2200 can be rotationally indexed (as indicated by arrow labeled R) during retraction of the cutter 120. Motor 500 powers rotation of lead screw 510 to translate nut 520, cutter carriage 530, and cutter 120 proximally, thereby opening tissue aperture 114 in cannula 100. As nut 520 travels proximally, the tab extension 522 pushes the pawl sled 2360 in a proximal direction, causing pawl 2362 to engage teeth 2354 and push "upward" on teeth 2354, causing manifold gear 2350 (and so manifold 2300) to rotate in the direction "R" shown in FIG. 5. The tissue holder 2200 rotates with the manifold 2300, and is positioned to have an empty recess or compartment aligned with port 2057 and sample transfer tube 2030.

In an alternative embodiment, rather than employing a pawl mechanism to index the manifold 2300, the manifold 2300 and tissue holder 2200 can be rotated based on a rotational position of the tissue receiving aperture 114. For instance, the cannula 100 may be rotatable with respect to the biopsy device to position the aperture 114 at a desired o'clock position, such as with a thumbwheel. U.S. Pat. No. 6,602,203, incorporated herein by reference, discloses a thumbwheel for rotating a tissue receiving aperture. If desired, the manifold 2300 and tissue holder 2200 can be configured to be rotated concomitantly with rotation of the aperture 114, so that each tissue holding recess or compartment on the tissue holder 2200 corresponds to a specific o'clock position of the aperture 114 during tissue sampling. In another alternative embodiment, motor 500 or a separate motor can be provided to rotate the tissue holder 2200 and manifold 2300. Alternatively, manifold 2300 may be rotated using any other suitable components, features, devices, or techniques.

Tissue holder 2200 may additionally or alternatively rotate a predetermined amount upon translation of the cutter 120, such as when the cutter 120 is advanced or retracted, so that with each cutter 120 stroke, the rotatable manifold 2300 repositions the tissue holder(s) 2200 supported on the manifold 2300, such that the tissue holders 2200 are "clocked" to receive the tissue sample 42 severed during that cutter 120 stroke. In one embodiment, a switch or lever (e.g., lever 2040) can be employed to allow selection of the direction of rotation of the rotatable manifold in either the clockwise or counter clockwise direction. By switching the lever, the entry point of the tissue sample into the tissue storage assembly can also be changed. For instance, the entry point of the tissue samples may be offset from a twelve o'clock position (straight up). In one embodiment, the lever can be employed to select the tissue entry point to be at either about a 2 o'clock or about a 10 o'clock position, so that the entry of the samples into the assembly can be seen through a clear cover 2010 of the tissue storage assembly 2000 by an operator using the biopsy device 10 in a stereotactic environment where the biopsy device 10 may be positioned close to the surface of the underside of the stereotactic table or elsewhere.

Figure 9:
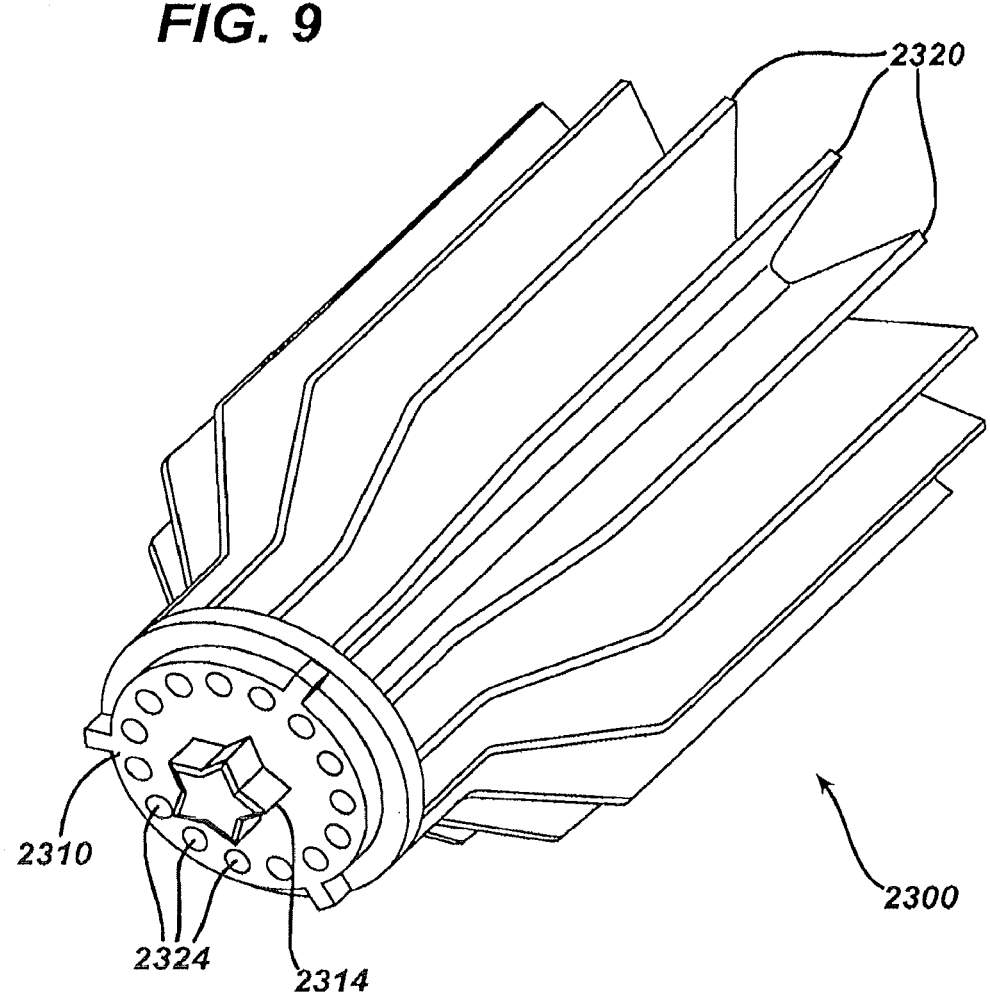
FIG. 9 is a schematic illustration of a manifold having radially extending fins and vacuum ports for conveying vacuum between adjacent fins.

FIG. 6 provides an enlarged illustration of the tissue storage assembly 2000 of the present example. FIG. 7 provides an exploded view of components of the tissue storage assembly 2000. FIG. 8 provides a cross-sectional illustration of components of the tissue storage assembly 2000. FIG. 9 is a schematic illustration of a manifold 2300 having radially extending fins 2320 and vacuum ports 2324 for conveying vacuum between adjacent fins.

Referring to FIGS. 6-8, the tissue sample assembly 2000 of the present example can comprise a plurality of tissue holders 2200. In FIG. 7, the tissue sample assembly comprises three sample holders designated 2200A, 2200B, and 2200C. The tissue holders 2200A-C are releasably carried by the manifold 2300. Each tissue holder 2200 can be removed from the biopsy device 10 by removing the cover 2010 and lifting or sliding the holder 2200 off of the manifold 2300 with the tissue samples 42 held in place on the tissue holder 2200.

In the embodiment shown in FIGS. 6-8, each of the tissue holders 2200A-C can extend about one hundred and twenty degrees around the circumference of the manifold 2300. Alternatively, tissue holders 2200AA-C may extend to any other suitable range (e.g., approximately 90 degrees, approximately 180 degrees, approximately 360 degrees, etc.). Each of the tissue holders 2200A-C of the present example is shaped or otherwise formed to receive and hold a plurality of tissue samples 42 in spaced apart, sequenced order. In FIG. 7, each tissue holder 2200A-C is in the form of a flexible tissue sample strip, and each tissue sample strip includes a plurality of recesses 2204, each recess 2204 for receiving a respective tissue sample 42.

Referring to FIGS. 6-9, the manifold 2300 can include a plurality of radially extending projections, such as radially extending fins 2320. The tissue holders 2200A-C can be shaped or otherwise formed to engage the fins 2320, such that the fins 2320 prevent circumferential motion of the holders 2200A-C relative to the manifold 2300, and such that the fins 2320 maintain the three tissue holders 2200A-C in position on the manifold 2300. When the tissue holders 2200A-C are seated on the manifold 2300, each recess 2204 can be positioned between a pair of adjacent fins 2320 of the manifold 2300. Alternatively, any suitable structure or feature other than fins 2320, radially extending or otherwise, may be provided by manifold 2300.

The tissue sample holders 2200A-C can be formed from thin polymeric sheet stock or using other materials, structures, and techniques. If desired, the tissue sample holders 2200A-C can be formed of a material that is generally radiotransparent (generally transparent to X-rays). In one embodiment, the sample holders 2200A-C can be formed of polypropylene having a thickness of about 0.015 inch or any other suitable thickness. The sample holders 2200A-C can have a radially inward facing surface 2203 and a radially outward facing surface 2205 (FIG. 8). The sample holders 2200A-C can be formed (such as by molding, vacuum forming, or pressing, etc.) to have tissue receiving recesses 2204 on the radially outward facing surface 2205 of the strips, each recess 2204 having a floor 2205, radially outward extending sidewalls 2206, and a proximal back wall 2208. Each recess 2204 can be positioned between a pair of adjacent manifold fins 2320 when the sample holder 2200A-C is seated on the manifold 2300. Each sample holder 2200A-C can also include a distally extending lip 2260.

Alternatively, sample holders 2200A-C can be formed to receive tissue samples on a radially inward facing surface 2203 of the sample holders 2200A-C or in some other suitable fashion.

Vacuum openings 2212, 2214, such as in the form of holes or slots, can be provided in the sample holders 2200A-C to communicate vacuum from the manifold 2300 through the sample holder 2200A-C, to convey tissue samples 42 from sample transfer tube 2030 to recesses 2204. For instance, vacuum openings 2214 can extend through the sidewalls 2206, and vacuum openings 2212 can extend through the floor 2205. Alternatively, any other structures in any suitable location may be used to permit fluid communication through sample holders 2200A-C.

Referring to FIGS. 8 and 9, the manifold 2300 can include fins 2320 extending from a generally disc shaped distal end plate 2310. The distal face of the end plate 2310 includes a spline feature 2314 for mating with a complementary recess (not shown) in the manifold gear 2350. The end plate 2310 also includes a plurality of vacuum ports 2324 extending through the end plate 2310, each port 2324 positioned to direct vacuum between an adjacent pair of fins 2320.

Vacuum provided from a vacuum source (e.g., from vacuum pump 4010, described below) and communicated to vacuum port 2060 in proximal cover 2050 is directed through cover 2050 to one of a plurality of passageways 2352 extending through the gear 2350. Each passageway 2352 extending through the manifold gear 2350 can be aligned with an associated vacuum port 2324 in the manifold end plate 2310 when the spline feature 2314 mates with the manifold gear 2350. Accordingly, vacuum provided at port 2060 is directed through cover 2050 to a passageway in the gear 2350, and then through a vacuum port 2324 in manifold 2300, to be directed between a pair of adjacent fins 2320. The direction of airflow provided by the sample storage vacuum supply is illustrated by arrows in FIG. 8.

In the above-described embodiment, the tissue holder 2200 comprises a plurality of sample holders 2200A-C. Alternatively, the tissue holder 2200 can comprise a single piece, such as in the form of a continuous ring extending three hundred and sixty degrees around the manifold 2300, or as a single strip extending substantially three hundred sixty degrees around the manifold. Alternatively, any other suitable structures, features, or devices may be used to hold tissue samples 42.

Figure 10:
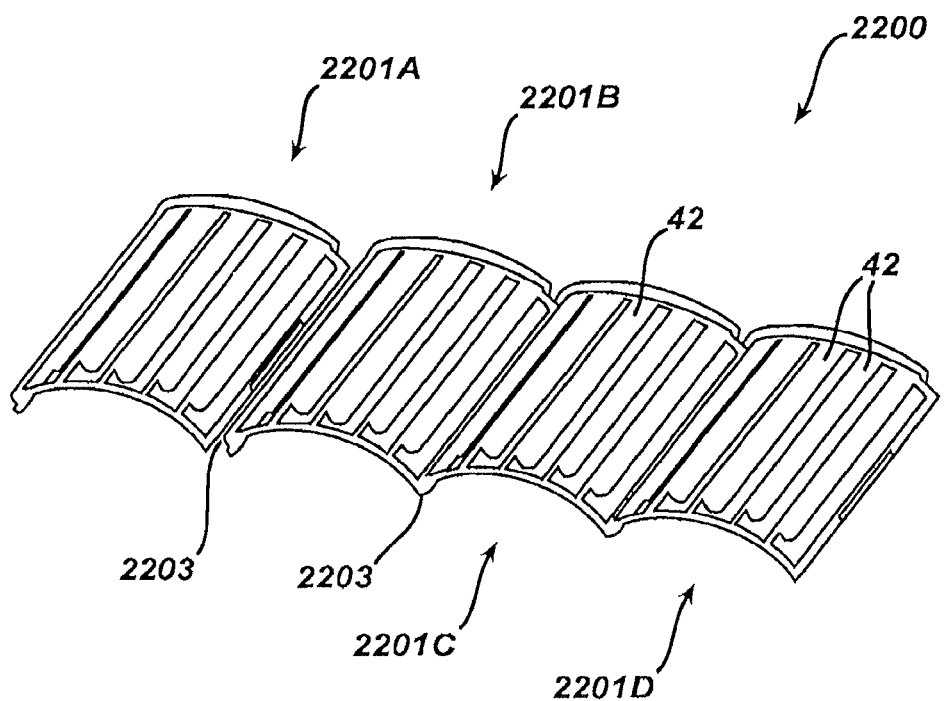
FIG. 10 illustrates an alternative embodiment of a tissue holder

FIG. 10 illustrates an alternative embodiment of a tissue sample holder 2200. In FIG. 10, a sample holder 2200 comprises a single strip comprising four segments 2201A-D, with adjacent pairs of the segments 2201A-D being joined together at a flexible hinges 2203. Each segment 2201A-D can have a generally arcuate shape encompassing about 90 degrees, with a generally convex outer surface having a plurality of recesses, each recess for holding a tissue sample.

The holder 2200 of this example, which can be radiotransparent or have other properties, can be removed from the tissue storage assembly 2000 with the tissue samples 42 held in spaced apart, sequenced order on the tissue holder 2200. The samples 42 can be tested and/or prepared for testing without removing the samples 42 from the holder 2200, and without disturbing the order of the samples 42 and/or without touching the individual samples 42, such as by placing the samples 42 and holder 2200 in any suitable test equipment or in a suitable test preparation fluid.

For example, if a patient is being examined for microcalcifications, a specimen radiograph can be performed on the samples 42 while the samples 42 are positioned on the tissue holder 2200. The specimen radiograph obtained is checked for microcalcifications. Those samples 42 on the tissue holder 2200 that exhibit microcalcifications can be removed from the tissue holder 2200, if desired. The tissue holder 2200, any tissue samples 42 remaining on the tissue holder 2200, and any tissue samples 42 that contain microcalcifications, can be immersed together in FORMALIN liquid to prepare the samples for pathology. Alternatively, the tissue holder 2200 together with the tissue samples 42 held on the tissue holder 2200 may be immersed together in saline or a suitable liquid preparation agent. Of course, tissue samples 42 may be subject to any other suitable processing, either while still on tissue holder 2200 or otherwise.

Figure 11:
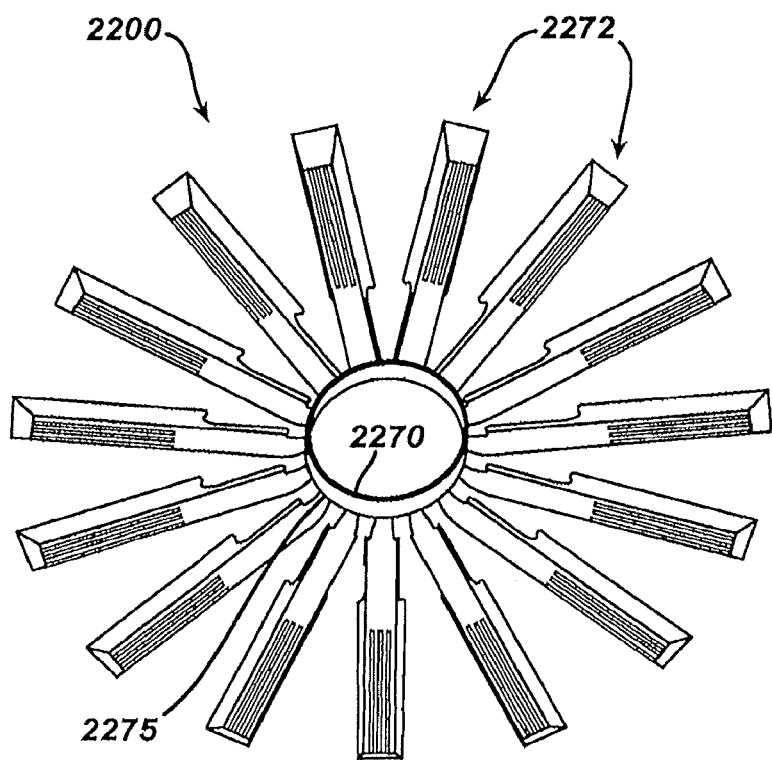
FIG. 11 illustrates another alternative embodiment of a tissue holder.
Figure 11A:
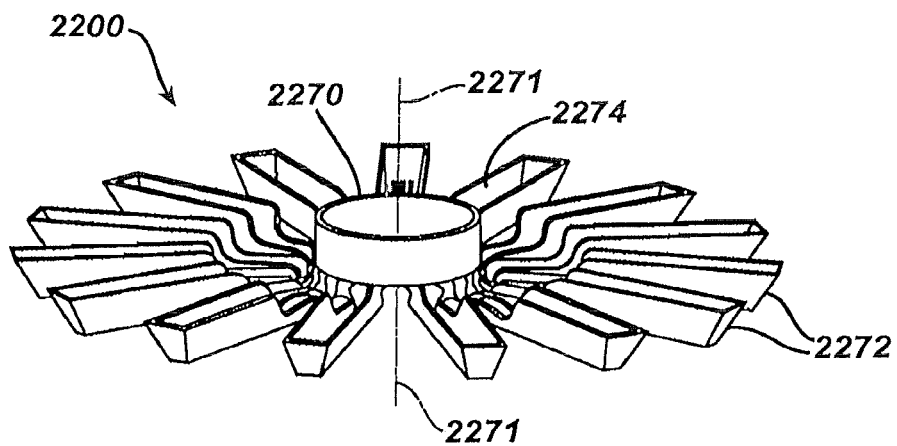
FIG. 11A illustrates a tissue holder of FIG. 11 in a relatively flat configuration.

FIGS. 11 and 11A illustrate another embodiment of a tissue sample holder 2200. In FIG. 11, the sample holder 2200 comprises a plurality of arms 2272 extending radially from a hub 2270. The hub 2270 can have a generally cylindrical shape and can be sized to fit over an end of a manifold 2300. The arms 2272 can be sized and spaced to fit between adjacent fins 2320 of the manifold 2300. The arms 2272 can each include a tissue receiving compartment 2274, which can be integrally formed in the arm 2272 itself, or alternatively, be a separate piece joined to the arm 2272. Tissue receiving compartments 2274 provide a cup-like or recessed configuration in the present example, though other configurations may be provided. Each arm 2272 can include one or more vacuum openings for communicating vacuum from the manifold 2300 to the tissue receiving compartment 2274.

Each arm 2272 can be joined to the hub at a hinge 2275. Each hinge 2275 can be a flexible "living" hinge, formed for instance, from a thin flexible strip of the material from which the arms 2272 are formed. Alternatively, other configurations may be used. The flexible hinge 2275 of the present example permits the arms 2272 to folded radially inward to extend generally parallel to the longitudinal axis 2271 of the hub 2270 when the holder 2200 is disposed in the tissue storage assembly 2000. When the holder 2200 is removed from the tissue storage assembly 2000, the flexible hinge 2275 of the present example permits the arms 2272 to folded radially outward to a flatter configuration, such as is shown in FIG. 11A.

The tissue holder 2200 can include indicia (e.g. letters, numbers, symbols, etc.) that are visible and/or radiopaque. For instance, the indicia can be used to identify each individual tissue holding recess or compartment 2274 on the tissue holder 2200. Each recess or compartment 2274 can have a unique number or symbol associated with it, where the number or symbol is formed or printed on the holder 2200 to be visible to the naked eye and/or radiopaque. Accordingly, when the tissue holder 2200 is withdrawn from the biopsy device 10, the individual tissue samples 42 can be uniquely identified on the holder 2200 both visibly and/or under x-ray.

If desired, the biopsy device 10 can include a display 6000 for indicating the number of tissue samples 42 cut as the biopsy device 10 is operated. For instance, the biopsy device 10 or the control unit 5000 can include a display 6000, such as an LEI) display 6000, that indicates the number of tissue samples 42 that have been severed and stored. Additionally, the LED display can include a diagrammatic display that indicates the location from which each sample 42 is taken relative to a reference. For instance, the display 60000 can indicate the "o'clock" position at which each sample 42 is taken relative to an initial 12 o'clock (straight up) position of the tissue aperture 114. Alternatively, the LED display 6000 can indicate a position for each compartment or recess 2274 on the tissue holder 2200, with the LED display 6000 indicating if a tissue sample 42 has been deposited in a particular compartment or recess 2274, or at a particular location around the circumference of the tissue holder 2200. Alternatively, a display 6000 may be incorporated with biopsy device 10 in any other suitable way and location, and may display any desired information.

FIG. 12 illustrates an alternative tissue storage device 2700 that can be used to hold tissue samples 42 in an end-to-end configuration. FIG. 12A is a cross-sectional view taken along lines 12A-12A. FIG. 12B is a sectional view taken along a length of a portion of the storage device 2700. The storage device 2700 of this example includes a flexible, coiled tissue sample holder 2710, which can be formed of thin-walled, flexible tubing, such as an extruded tubing. The tissue sample holder 2710 includes three lumens 2712, 2714, 2716 extending alongside each other along the length of the coiled tissue sample holder 2710.

The sample holder 2710 of this example includes a tissue sample lumen 2712 for receiving tissue samples 42 in an end-to-end sequence, a vacuum supply lumen 2714, and a vacuum control lumen 2716 positioned between and extending alongside of lumen 2712 and lumen 2714. A flexible, elongated control member 2718 is positioned in control lumen 2716. When the elongated control member 2718 is fully inserted in the control lumen 2716, the control member 2718 serves to block a series of cross flow ports 2719, which are disposed at spaced intervals along the length of the vacuum control lumen 2716. The cross flow ports 2719 can be spaced apart along the length of the vacuum control lumen 2716 a distance generally equal to or slightly larger than the maximum length of a tissue sample 42 severed by the cutter 120 of the biopsy device 10. Control member 2718 can be withdrawn from lumen 2716 in the direction shown, in incremental steps, to permit vacuum in vacuum supply lumen 2714 to be communicated to sample lumen 2712. Each time the control member 2718 is incrementally withdrawn, a pair of cross flow ports 2719 in vacuum control lumen 2716 are uncovered to provide vacuum in sample lumen 2712. Alternatively, a vacuum may be selectively communicated to a sample lumen 2712 using any other suitable structures, features, devices, or techniques.

In the present example, tissue sample lumen 2712 can be connected directly or indirectly to the sample transfer tube 2030. Lumen 2714 can be connected to a source of vacuum (e.g., vacuum control module 5000). The control member 2718 can be withdrawn manually, or alternatively, can be automatically withdrawn by a winding mechanism (not shown) associated with the biopsy device 10.

Figure 13:
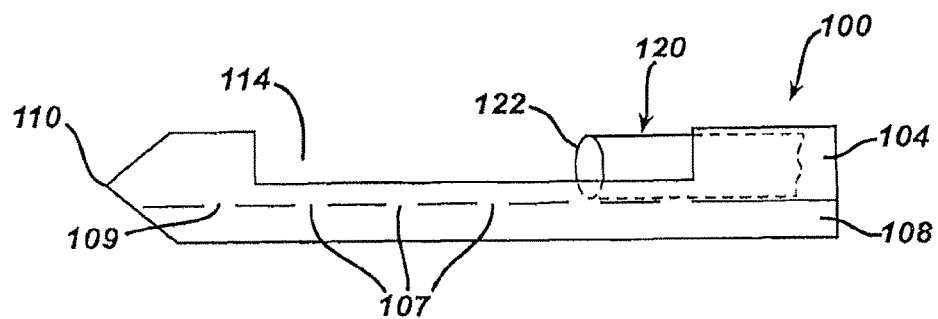
FIG. 13 is a schematic illustration of the distal portion of an exemplary cannula.
Figure 14:
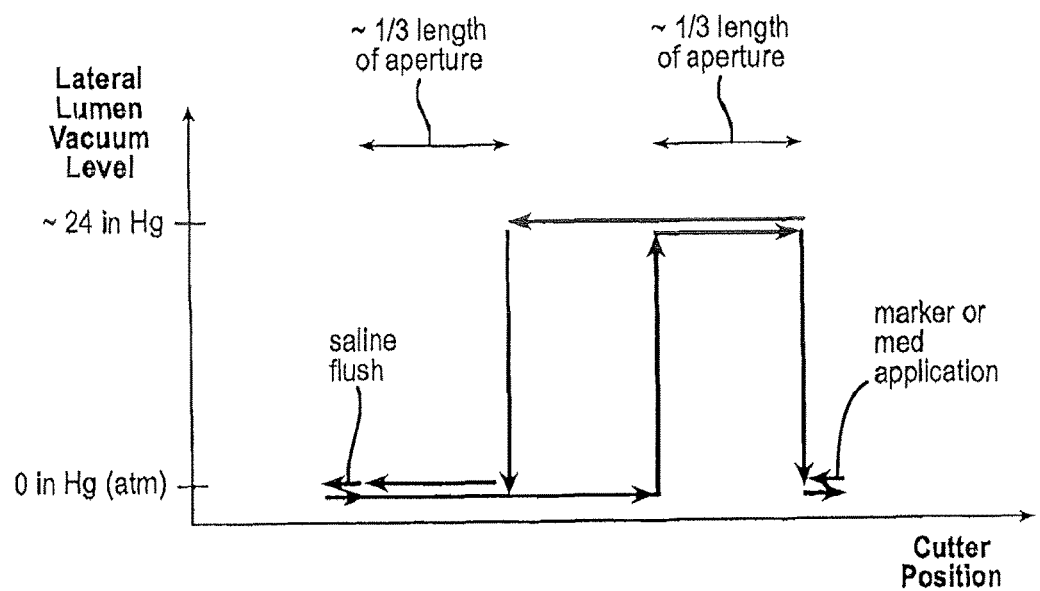
FIG. 14 is a schematic illustration of the vacuum level provided in a vacuum lumen as a cutter is advanced and retracted in a cutter lumen relative to a tissue receiving aperture.

FIG. 13 provides a schematic illustration of the distal portion of cannula 100, and FIG. 14 provides a schematic illustration of the vacuum level that can be provided in vacuum lumen 108 as cutter 120 is advanced and retracted in cutter lumen 104 relative to tissue receiving aperture 114. FIG. 13 illustrates passageways that can be provided in the internal structure of cannula 100 to provide flow communication between vacuum lumen 108 and cutter lumen 104. Passageways 107 are disposed generally beneath aperture 114, and passageway 109 is disposed distal of aperture 114.

Figure 15:
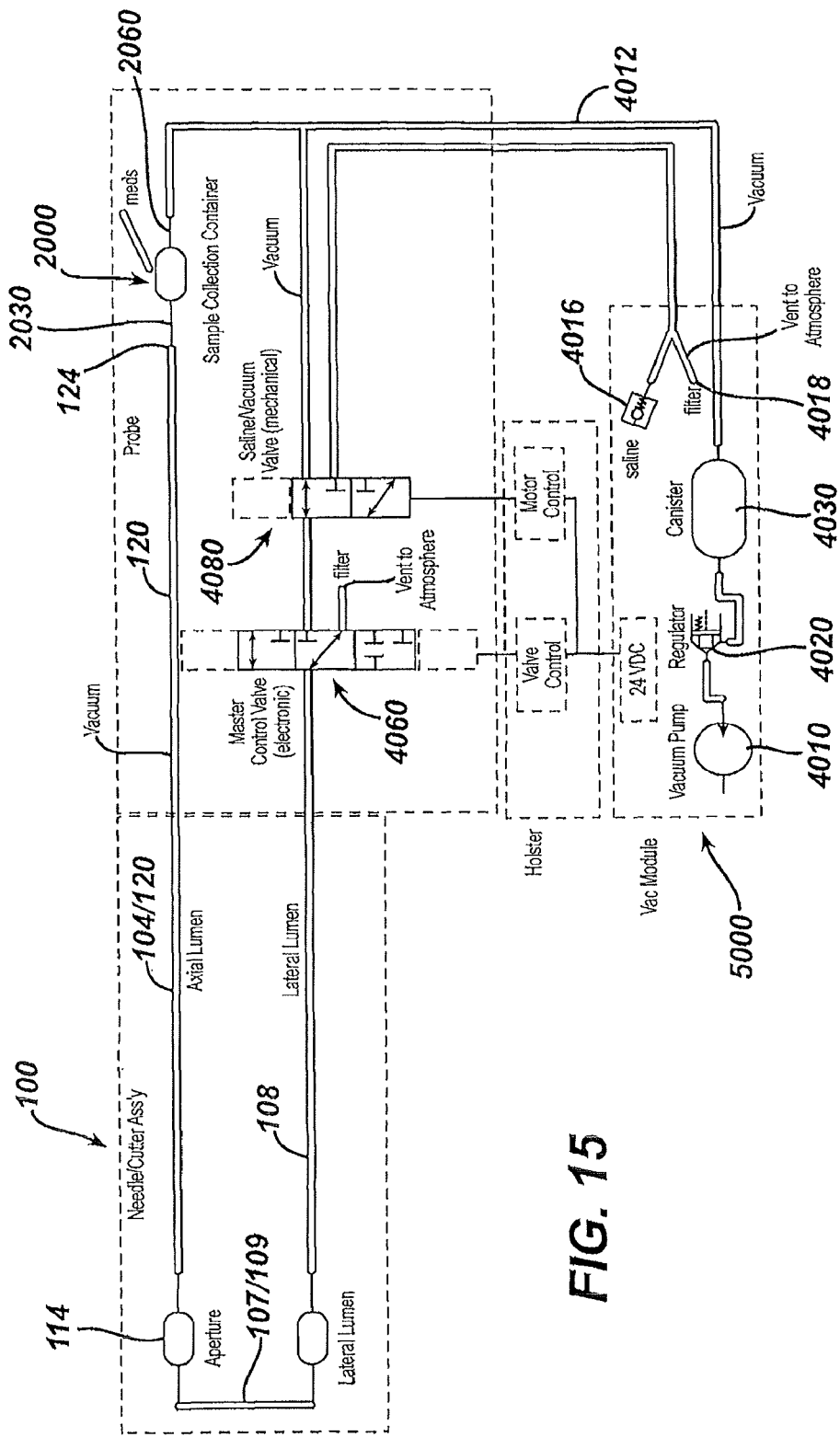
FIG. 15 is a schematic illustration of a pneumatic control configuration that may be used with a biopsy device.

FIG. 15 is a schematic illustration of a pneumatic configuration that can be used with the biopsy device 10 of the present example. The pneumatic system can include a vacuum pump 4010, a regulator 4020, a vacuum canister/reservoir 4030, a master control valve 4060, and a saline/vacuum valve 4080.

The vacuum provided by the vacuum pump 4010 can be directed through vacuum line 4012, through tissue storage assembly 2000, to cutter 120 and cutter lumen 104 without valving, so that the vacuum provided to the interior of cutter 120 and to cutter lumen 104 of cannula 100 is always "on" when vacuum pump 4010 is operating. Alternatively, one or more valves or other features or mechanisms may be provided along such a fluid path. The pneumatic circuit for vacuum lumen 108 includes two valves 4060, 4080. Valve 4080 can comprise a 3-port/2-position valve, with two input ports. One input port can be connected to vacuum line 4012, and the other input port can be connect to a source of saline 4016 (or alternatively vented to atmospheric pressure through filter 4018). The output port of valve 4080 communicates with an inlet port of master valve 4060.

The position of the valve 4080 is configured to correspond to the position of the cutter 120. When the cutter 120 is retracted proximally (e.g., such that tissue aperture 114 is open), the valve 4080 communicates vacuum to the master control valve 4060. When the cutter 120 is advanced distally (e.g., such that tissue receiving aperture 114 closed), the valve 4080 communicates saline to the master control valve 4060. Alternatively, if saline is not available, or not desired, then valve 4080 communicates atmospheric air via filter 4018 to the master control valve 4060. The valve 4080 can be actuated in any suitable manner, including with a solenoid, a motor, by a mechanical link to the cutter 120, or otherwise. The valve 4080 can be spring loaded in one position, and movement of the cutter 120 (such as movement of the cutter 120 to the distal position) can be employed to change the valve 4080 position.

The master control valve 4060 can comprise a 3-port/3-position valve. One input port can be connected to the output port of the valve 4080. The second input port can be vented to filtered atmospheric air. The output port of the valve 4060 can be connected to the proximal end of vacuum lumen 108 of cannula 100. The position of valve 4060 can be controlled by the operator of the biopsy device 10 using one or more user control interfaces, such as the control buttons listed in FIG. 16. The control buttons (not shown on device 10), can be located at any convenient position on the body of the biopsy device 10, including for instance on handpiece 30, or elsewhere (e.g., on vacuum control module 5000). The valve 4060 can be actuated by a solenoid, motor, via a link to the cutter 120, or otherwise.

Of course, the pneumatic circuit shown in FIG. 15 is merely illustrative, and any other suitable circuit, including different components, arrangements of components, and operation of components, may be used.

FIG. 16 illustrates multiple control states that can be employed in controlling the biopsy device 10. With reference to FIG. 16, With reference to FIG. 8, the "Ready State" of biopsy device 10 corresponds to the cutter 120 being advanced to its distal most position and tissue aperture 114 being closed. In the Ready State, the valve 4080 communicates saline to the master control valve 4060 and the master control valve is positioned to seal off (close) its other ports, including the output port communicating with vacuum lumen 108. By closing the port to the lateral lumen 108 while in the Ready State, airflow through the device may be minimized, which may allow the pump 4010 to more easily maintain the desired vacuum level at the vacuum canister 4030.

When the operator depresses the "Sample" button 170 in the present example, the cutter motor is activated to cause the cutter 120 to retract proximally. As the cutter retracts, the valve 4080 changes position to communicate vacuum to the master control valve 4060. At the same time, the master control valve changes position to communicate a vacuum to the vacuum lumen 108. With the tissue aperture 114 open, vacuum from vacuum pump 4010 is applied to the cutter 120 (such as via the tissue storage assembly 2000) and cutter lumen 104 (via the cutter 120), as well as to the vacuum lumen 108 (via the valves 4080 and 4060). Vacuum applied to both cutter lumen 104 and vacuum lumen 108 assists in prolapsing tissue into aperture 114 of cannula 100.

After maintaining this vacuum state for a second or more to ensure tissue has prolapsed into aperture 114, the cutter 120 is advanced distally (and simultaneously rotated) to close the aperture 114 and sever a tissue sample 42 in the distal portion of the hollow cutter 120. As the cutter 120 advances distally, the cutter 120 can contact or otherwise actuate the valve 4080 to change the valve position to communicate saline to the master control valve 4060. Also, as the cutter 120 advances, a microprocessor can be employed to change the master control valve 4060 position to communicate filtered atmospheric air to vacuum lumen 108, which in turn is communicated via passageways 107, 109 to the distal face of the severed tissue sample 42 positioned in the distal portion of hollow cutter 120. The atmospheric air on the distal face of the tissue sample provides a proximal pushing force on the tissue sample 42, while the vacuum provided in cutter 120 (via the tissue storage assembly 2000) provides a proximally directed pulling force on the severed tissue sample 42. The resulting proximally directed force on the tissue sample 42 conveys the tissue sample 42 through the hollow cutter 120 into tissue storage assembly 2000. Of course, any other suitable structures or techniques may be used to capture a tissue sample 42 and communicate it to a tissue storage assembly 2000.

In an alternative embodiment, the microprocessor can be employed to change the position of master control valve 4060 to first communicate saline to vacuum lumen 108 for a predetermined period of time, and then change the valve's position to communicate atmospheric air to the lumen 108. Accordingly, a fixed volume of saline can be delivered via passageways 107,109 to the distal end of hollow cutter 120, thereby assisting in moving the severed tissue sample proximally through hollow cutter 120 to tissue storage assembly 2000. The control system can be programmed to return to the Ready State after a predetermined period of time (e.g., one or more seconds).

The biopsy device operator can depress the "Clear Probe" button 172 while in the Ready State (e.g., after having operated the "Sample" button 170 to sever tissue) in order to direct a microprocessor control to cause the cutter 120 to reciprocate slightly to open and close aperture 114 a fraction of an inch (e.g. 0.2 inches), or to any suitable degree. This reciprocation of cutter 120 can be effective to dislodge the tissue sample 42 or otherwise free the sample 42 so that the sample 42 can travel freely through hollow cutter 120. While the cutter 120 is reciprocating, the vacuum control valve 4060 can be repositioned to communicate saline to the vacuum lumen 108 and through passageways 107, 109 to provide a pushing force on the distal face of the tissue sample 42. After a predetermined period of time, the microprocessor can return the pneumatic system to the Ready State.

The operator can depress and release the "Aspirate/Insert" button 174 when the device is in the Ready State to insert medication or a tissue marker into the tissue being sampled or into the site from which a tissue sample has been or will be taken. When the button 174 is depressed in this example, the cutter 120 moves proximally to open aperture 114. The position of the master control valve 4060 is changed to communicate atmospheric air to the vacuum lumen 108. Depressing the "Aspirate/Insert" button 174 also turns off the vacuum (such as by either turning off the pump 4010 or opening regulator 4020 to vent pump 4010 outlet to atmosphere, etc.). The tissue marker applier (or medication) can be fed into the proximal end of the cannula 100 through hollow cutter 120, such as via the tissue storage assembly 2000 or otherwise, with the marker (or medication) being then deployed through the open aperture 114 in cannula 100. After the marker or medication has been deployed, the user may press any button, which may advance the cutter 120 to return to the Ready State with the master control valve 4060 positioned up.

The operator can depress and hold the "Aspirate/Insert" button 174 to aspirate fluid in the vicinity of aperture 114. When the operator depresses the button 174 in this example, the cutter 120 moves proximally to open aperture 114. With the cutter positioned proximally, the valve 4080 communicates vacuum to the master control valve 4060, and the master control valve 4060 is positioned to communicate vacuum to the vacuum lumen 108. Accordingly, vacuum is applied to both the lumen 108 and the cutter lumen 104 (because vacuum is provided continuously through cutter 120 to lumen 104 while the pump 4010 operates in this example). The vacuum provided to lumen 104 and lumen 108 aspirates any liquid near the aperture 114. When the Aspirate/Insert button 174 is released, the pneumatic system is controlled to return the Ready State. The cutter 120 is advanced to close aperture 114. As the cutter 120 is advanced in this example, the master control valve 4060 is positioned to communicate filtered atmospheric air to the vacuum lumen 108. Once the aperture 114 is closed, the master control valve 4060 is positioned to close all its ports to attain the Ready State. As with other operational sequences described herein, the foregoing operational sequence is merely illustrative, and any other suitable operational sequences may be used in addition to or in lieu of those explicitly described herein.

The length of the vacuum line 4012 from the control module 5000 housing the vacuum pump 4010 to the biopsy device 10 can be relatively long (as much as 20 feet or more in some cases) in order to accommodate movement of the biopsy device 10 in the operating room, or due to limitations of the position of the control module 5000 in magnetic resonance imaging environments. Of course, vacuum line 4012 may be of any desired length. In the present example, the vacuum line 4012 can account for a considerable portion of the flow volume that needs to be supplied or maintained by the vacuum pump 4010 and vacuum canister 4030 when the tissue aperture 114 is open. Placing the saline vacuum valve 4080 and the master control valve 4080 at the distal end of the vacuum line 4012 (the end associated with the biopsy device 10) instead of in the biopsy vacuum control unit 5000 may mean that a smaller vacuum pump 4010 and a smaller vacuum canister 4030 can be used. In some conventional biopsy devices, valving may be placed in the control unit that includes the vacuum pump, and the control unit is may be mounted on wheels due to its weight and size. In FIG. 16 the valves 4060, 4080 are shown disposed in the biopsy device 10. The valves 4060, 4080 can be disposed in a disposable probe portion that includes the cannula 100 and cutter 120 (e.g. handpiece 30) and/or is a non-disposable (e.g., holster) portion of the biopsy device 10. Such a valve placement may allow a relatively low weight diaphragm vacuum pump 4010 having a flow rate of about 18 liters per minute to be used, as compared to a conventional pump and valve arrangement requiring more than 80 liters per minute. Of course, any desired vacuum pump having any desired properties may be used.

Similarly, the vacuum canister 4030 can be relatively small, with a volume of less than about 300 cubic centimeters, as compared to a conventional vacuum canister having a volume storage capacity of 1200 cc's or more. As a result, a relatively lightweight, hand-portable vacuum control module 5000 can be employed. The vacuum control module 5000 (FIG. 15) can weigh less than 25 pounds, can be carried by one hand, and can have height, width, and length dimensions each less than about 1.5 feet. Alternatively, vacuum canister 4030 and control module 5000 may have any other suitable capacity, size, weight, or other properties.

If desired, a foot pedal (not shown) or remote keypad (not shown) can be employed to provide control input or instructions to the biopsy device 10 directly and/or to the vacuum control module 5000. The foot pedal and remote keypad can be tethered (e.g., with one or more wires extending from the foot pedal/keypad to the vacuum control module 5000, etc.). Alternatively, "wireless" communication between the foot pedal/keypad and the control module 5000 and/or the biopsy device 10 can be employed. For instance, wireless "Bluetooth" communication and associated hardware and software can be employed to provide wireless control signals to the vacuum control module 5000 and/or the biopsy device 10 without requiring a "line of sight" for signal transmission and reception. Alternatively, an infrared transmitter and receiver can be employed to send and receive control signals. Other ways in which communication may be provided between components of a biopsy system (e.g., between a pedal/keypad and control module 5000), whether wired, wireless, or otherwise, will be apparent to those of ordinary skill in the art in view of the teachings herein.

While preferred embodiments of the present invention have been shown and described herein, it will be obvious to those skilled in the art that such embodiments are provided by way of example only. Numerous variations, changes, and substitutions will now occur to those skilled in the art without departing from the spirit and scope of the appended claims. Additionally, each element described in relation to the invention can be alternatively described as a means for performing that element's function.

What is claimed is:

1. A method of using a biopsy device to collect tissue samples, comprising;
   (a) providing the biopsy device, the biopsy device comprising:
     (i) a body,
     (ii) a cannula extending distally from the body, wherein the cannula defines a transverse tissue receiving aperture,
     (iii) a cutter translatable relative to the cannula, the cutter having a proximal end and a distal end, wherein the distal end of the cutter is operable to sever tissue received in the transverse tissue receiving aperture of the cannula,
     (iv) a tissue storage assembly, the tissue storage assembly including a rotatable tissue holder, wherein the rotatable tissue holder includes a plurality of compartments arranged in an angularly spaced array, wherein the compartments are configured to receive tissue samples severed by the cutter,
     (v) a flexible tube disposed between the tissue storage assembly and the cutter, wherein the flexible tube is configured to communicate tissue samples severed by the cutter to the tissue storage assembly,
     (vi) a display, wherein the display includes a visual representation of the rotatable tissue holder of the tissue storage assembly, and
     (v) a control unit, where the display is disposed on the control unit;
   (b) inserting the cannula in tissue;
   (c) translating the cutter relative to the cannula to sever a first tissue sample;
   (d) transporting the first tissue sample through the flexible tube to collect the first tissue sample in a first sample compartment of the tissue storage assembly;
   (e) depicting a representation of the collected first tissue sample through the visual representation of the rotatable tissue holder via the display;
   (f) rotating the rotatable tissue holder to position a second sample compartment of the tissue storage assembly to receive a second tissue sample;
   (g) translating the cutter relative to the cannula to sever a second tissue sample, (h) collecting the second tissue sample in the second sample compartment of the tissue storage assembly; and (i) adjusting the display to depict a representation of the collected second tissue sample through the visual representation of the rotatable tissue holder via the display.

2. The method of claim 1, wherein the visual representation of the rotatable tissue holder depicts rotation of the rotatable tissue holder.

3. The method of claim 1, wherein the visual representation of the rotatable tissue holder depicts all compartments of the plurality of compartments.

4. The method of claim 1, wherein the display is located on the body.

5. The method of claim 1, wherein the control unit is separate from the body.

6. The method of claim 1, wherein the display visually depicts the number of tissue samples acquired during a biopsy procedure.

7. The method of claim 1, wherein the tissue storage assembly further includes a transparent cover surrounding the rotatable tissue holder, wherein the rotatable tissue holder rotates within the cover.

8. The method of claim 1, wherein the tissue storage assembly further includes a cover, wherein the rotatable tissue holder rotates relative to the cover, wherein the cover includes a port, wherein the flexible tube is coupled with the port, wherein the flexible tube is further in communication with the cutter such that the flexible tube conveys severed tissue samples from the cutter to the port during the steps of transporting the first tissue sample or collecting the second tissue sample, wherein the port further conveys the severed tissue samples from the flexible tube to the rotatable tissue holder during the steps of transporting the first tissue sample or collecting the second tissue sample.

9. The method of claim 1, wherein the tissue storage assembly further includes a rotatable member releasably carrying the rotatable tissue holder.

10. The method of claim 1, further comprising a cannula firing assembly, wherein the cannula firing assembly includes:
(i) spring, and
(ii) a motor,
wherein the method further includes the step of moving the cannula distally via the spring.

11. A method of using a biopsy device to collect tissue samples, the method comprising the steps of:
(a) providing the biopsy device, where the biopsy device comprising:
(i) a body,
(ii) a cannula extending distally from the body, wherein the cannula defines a transverse tissue receiving aperture,
(iii) a cutter translatable relative to the cannula, the cutter having a proximal end and a distal end, wherein the distal end of the cutter is operable to sever tissue received in the transverse tissue receiving aperture of the cannula,
(iv) a tissue storage assembly, the tissue storage assembly including a rotatable tissue holder, wherein the rotatable tissue holder includes a plurality of compartments arranged in an angularly spaced array, wherein the compartments are configured to receive tissue samples severed by the cutter,
(v) a flexible tube disposed between the tissue storage assembly and the cutter, wherein the flexible tube is configured to communicate tissue samples severed by the cutter to the tissue storage assembly,
(vi) a display, wherein the display includes a visual representation of the rotatable tissue holder of the tissue storage assembly, and
(v) a control unit, wherein the display is disposed on the control unit;
(b) inserting the cannula in tissue;
(c) translating the cutter relative to the cannula to sever a first tissue sample from tissue received within the transverse tissue receiving aperture defined by the cannula;
(d) transporting the first tissue sample through the flexible tube disposed between a tissue storage assembly and the cutter to collect the first tissue sample in a first sample compartment of a plurality of sample compartments defined by the rotatable tissue holder associated with the tissue storage assembly;
(e) depicting a representation of the collected first tissue sample through a visual representation of the rotatable tissue holder via the display;
(f) rotating the rotatable tissue holder to position a second sample compartment of the tissue storage assembly to receive a second tissue sample;
(g) translating the cutter relative to the cannula to sever a second tissue sample;
(h) collecting the second tissue sample in the second sample compartment of the tissue storage assembly; and
(i) adjusting the display to depict a representation of the collected second tissue sample through the visual representation of the rotatable tissue holder via the display.

12. The method of claim 11, wherein the step of adjusting the display to depict a representation of the collected second tissue sample includes depicting rotation of the rotatable tissue holder.

13. The method of claim 11, wherein the step of depicting a representation of the collected first tissue sample includes depicting all compartments of a plurality of compartments defined by the rotatable tissue sample holder.

14. The method of claim 11, wherein the step of depicting includes displaying the visual representation with the display disposed on the body of the biopsy device.

15. The method of claim 11, wherein the step of depicting includes displaying the visual representation with the display disposed on a control unit while the control unit is positioned separately from the body of the biopsy device.

16. The method of claim 11, further comprising continuously updating the display to indicate the number of samples that have been collected during the biopsy procedure.

17. The method of claim 11, further comprising visualizing the rotatable tissue holder through a transparent cover surrounding the rotatable tissue holder, further comprising rotating the rotatable tissue holder while the transparent cover surrounds the rotatable tissue holder.

18. The method of claim 11, wherein the step of rotating the rotatable tissue holder includes rotating the rotatable tissue holder relative to a cover, wherein the flexible tube is coupled with a port included within the cover such that such that the flexible tube conveys severed tissue samples from the cutter to the port during the step of transporting the first tissue sample or the step of collecting the second tissue sample, wherein the port further conveys the severed tissue samples from the flexible tube to the rotatable tissue holder during the step of transporting the first tissue sample or the step of collecting the second tissue sample.

19. The method of claim 11, wherein the step of transporting includes collecting the first tissue sample in the rotatable tissue holder, which is detachably attached to a rotatable member associated with the tissue storage assembly.

20. The method of claim 11, further comprising moving the cannula distally via a spring associated with a firing assembly of the biopsy device.

* * * * *